United States Patent
Yonemitsu et al.

(10) Patent No.: US 11,987,812 B2
(45) Date of Patent: May 21, 2024

(54) POPULATION OF CD3-NEGATIVE CELLS THAT EXPRESS CHEMOKINE RECEPTOR AND CELL ADHESION MOLECULE, USE OF THE SAME, AND METHOD FOR PRODUCING THE SAME

(71) Applicants: GAIA BioMedicine Inc., Fukuoka (JP); Yoshikazu Yonemitsu, Fukuoka (JP)

(72) Inventors: Yoshikazu Yonemitsu, Fukuoka (JP); Yui Harada, Fukuoka (JP)

(73) Assignees: GAIA BioMedicine Inc., Fukuoka (JP); Yoshikazu Yonemitsu, Fukuoka (JP)

( * ) Notice: Subject to any disclaimer, the term of this patent is extended or adjusted under 35 U.S.C. 154(b) by 891 days.

(21) Appl. No.: 17/041,061

(22) PCT Filed: Mar. 26, 2019

(86) PCT No.: PCT/JP2019/012744
§ 371 (c)(1),
(2) Date: Oct. 26, 2020

(87) PCT Pub. No.: WO2019/189115
PCT Pub. Date: Oct. 3, 2019

(65) Prior Publication Data
US 2021/0095250 A1   Apr. 1, 2021

(30) Foreign Application Priority Data
Mar. 27, 2018 (JP) ................................. 2018-059624

(51) Int. Cl.
| | | |
|---|---|---|
| *C12N 5/0783* | (2010.01) | |
| *A61K 35/17* | (2015.01) | |
| *A61P 35/00* | (2006.01) | |
| *C12N 5/00* | (2006.01) | |

(52) U.S. Cl.
CPC ............ *C12N 5/0646* (2013.01); *A61K 35/17* (2013.01); *A61P 35/00* (2018.01); *C12N 5/0081* (2013.01); *C12N 2501/2302* (2013.01)

(58) Field of Classification Search
None
See application file for complete search history.

(56) References Cited

U.S. PATENT DOCUMENTS

| | | |
|---|---|---|
| 9,404,083 B2 | 8/2016 | Yonemitsu et al. |
| 2003/0068306 A1 | 4/2003 | Dilber |
| 2013/0011376 A1 | 1/2013 | Peled et al. |
| 2014/0120072 A1 | 5/2014 | Yonemitsu et al. |

FOREIGN PATENT DOCUMENTS

| | | |
|---|---|---|
| EP | 2725100 A1 | 4/2014 |
| JP | 2013-027385 A | 2/2013 |
| JP | 2013-515497 A | 5/2013 |
| JP | 5572863 B2 | 8/2014 |
| WO | 2011/080740 A1 | 7/2011 |

OTHER PUBLICATIONS

Extended European Search Report dated Dec. 14, 2021, issued in the counterpart European patent application No. 19775565.5 (in English; 8 pages).
Examination Report dated Jan. 24, 2022, issued in the counterpart Australian patent application No. 2019242949 (in English; 3 pages).
Office Action dated Mar. 27, 2023, issued in counterpart TW application No. 108110602, with English translation. (9 pages).
Office Action dated Nov. 25, 2022 issued in counterpart TW application No. 108110602, with English translation. (8 pages).
Office Action dated Jun. 7, 2023, issued in counterpart CN application No. 201980022253.X, with English translation. (14 pages).
Search Report and Written Opinion, dated Jun. 25, 2019, issued in counterpart International Application No. PCT/JP2019/012744 (w/ English translation; 16 pages).
International Preliminary Report on Patentability, dated Oct. 8, 2020, issued in counterpart International Application No. PCT/JP2019/012744 (w/ English translation; 13 pages).
Office Action dated Jul. 24, 2018, issued in counterpart Japanese patent application No. 2018-059624 (w/ English machine translation; 6 pages).
Office Action dated Nov. 27, 2018, issued in counterpart Japanese patent application No. 2018-059624 (w/ English machine translation; 10 pages).
Office Action dated Apr. 2, 2019, issued in counterpart Japanese patent application No. 2018-059624 (w/ English machine translation; 6 pages).
Melero, I., et al., "T-Cell and NK-Cell Infiltration into Solid Tumors: A Key Limiting Factor for Efficacious Cancer Immunotherapy", Cancer Discovery, vol. 4, No. 5, pp. 522-526 (May 2014) (in English; 6 pages; cited in specification).
Jena, B., et al., "Redirecting T-cell specificity by introducing a tumor-specific chimeric antigen receptor", Blood, vol. 116, No. 7, pp. 1035-1044 (Aug. 2010) (in English; 10 pages, cited in specification).
Moon E. K., et al., "Expression of a Functional CCR2 Receptor Enhances Tumor Localization and Tumor Eradication by Retargeted Human T Cells Expressing a Mesothelin—Specific Chimeric Antibody Receptor", Clin. Cancer Res., vol. 17, No. 14, pp. 4719-4730 (Jul. 2011) (in English; 20 pages; cited in specification).

(Continued)

*Primary Examiner* — Robert M Kelly
(74) *Attorney, Agent, or Firm* — WHDA, LLP

(57) ABSTRACT

The present invention relates to an immunocyte having higher cytotoxic activity, and a pharmaceutical composition for NK cell therapies, for which high effect can be expected. The present invention provides a cell population including CCR5-positive, CCR6-positive, CXCR3-positive, and CD3-negative cells. The present invention provides the cell population, wherein the CCR5-positive, CCR6-positive, CXCR3-positive, and CD3-negative cells further highly express CD11c. The present invention provides a CCR5-positive, CCR6-positive, CXCR3-positive, and CD3-negative cell, which infiltrates into a solid tumor. The present invention also provides a pharmaceutical composition containing such a cell population and a pharmaceutically acceptable additive. The present invention further provides a method for producing the aforementioned cell population.

12 Claims, 11 Drawing Sheets

(56) References Cited

OTHER PUBLICATIONS

Lima M., et al., "Chemokine Receptor Expression on Normal Blood CD56+ NK-Cells Elucidates Cell Partners That Comigrate during the Innate and Adaptive Immune Responses and Identifies a Transitional NK-Cell Population", Journal of Immunology Research, vol. 2015, Article ID 839684, pp. 1-18 (2015) (in English; 18 pages; cited in specification).

Takahashi, E., et al., "Induction of CD16+ CD56bright NK cells with antitumour cytotoxicity not only from CD16-CD56bright NK cells but also from CD16-CD56dim NK cells", Scand. J. Immuno. vol. 65, No. 2, pp. 126-138 (2007) (in English; 13 pages; cited in ISR, IPRP, and Japanese patent application No. 2018-059624).

Berahovich, R. D., et al., "Evidence for NK cell subsets based on chemokine receptor expression", J. Immunol., vol. 177, No. 11, pp. 7833-7840 (2006) (in English; 8 pages; cited in ISR, IPRP, and Japanese patent application No. 2018-059624).

Poli, A., et al., "CD56bright natural killer (NK) cells: an important NK cell subset", Immunology, vol. 126, No. 4, pp. 458-465 (2009) (in English; 8 pages; cited in ISR, IPRP, and Japanese patent application No. 2018-059624).

Levi, I., et al., "Characterization of tumor infiltrating natural killer cell subset", Oncotarget, vol. 6, No. 15, pp. 13835-13843 (2015) (in English; 9 pages; cited in ISR and IPRP).

Saito, S., et al., "Ex Vivo generation of highly purified and activated natural killer cells from human peripheral blood", Hum. Gene Ther. Methods, vol. 24, No. 2, pp. 241-252 (2013) (in English; 12 pages; cited in ISR, IPRP, and Japanese patent application No. 2018-059624).

Saito, S. et al., "Supplementary Data", Human. Gene Therapy Methods, 2013, vol. 24, No. 4, pp. 1-2, cited in EP Extended European Search Report dated Dec. 14, 2021. (2 pages).

Office Action dated Aug. 22, 2022, issued in counterpart KR application No. 10-2020-7030870, with English translation. (6 pages).

[Figure 1A]
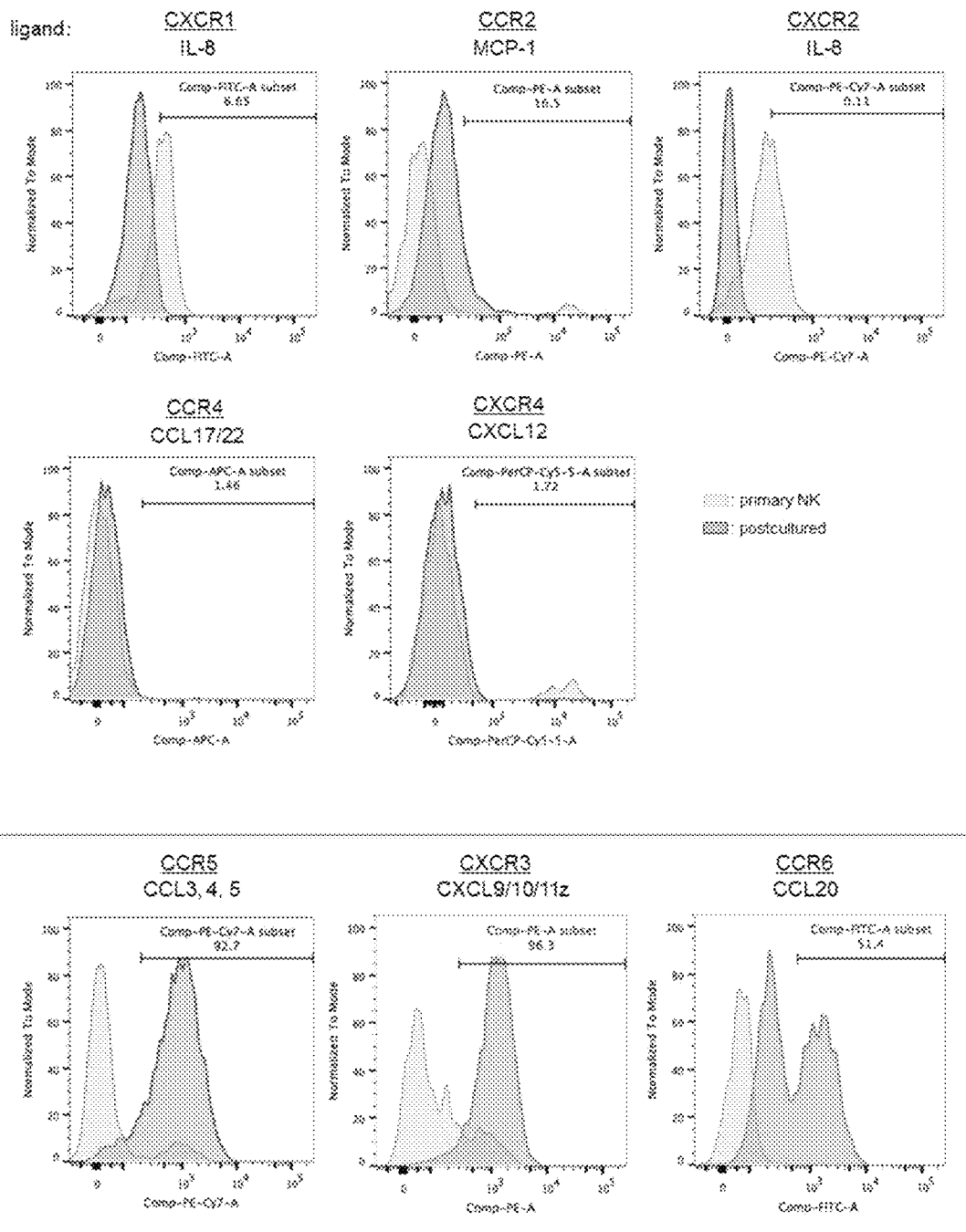

[Figure 1B]
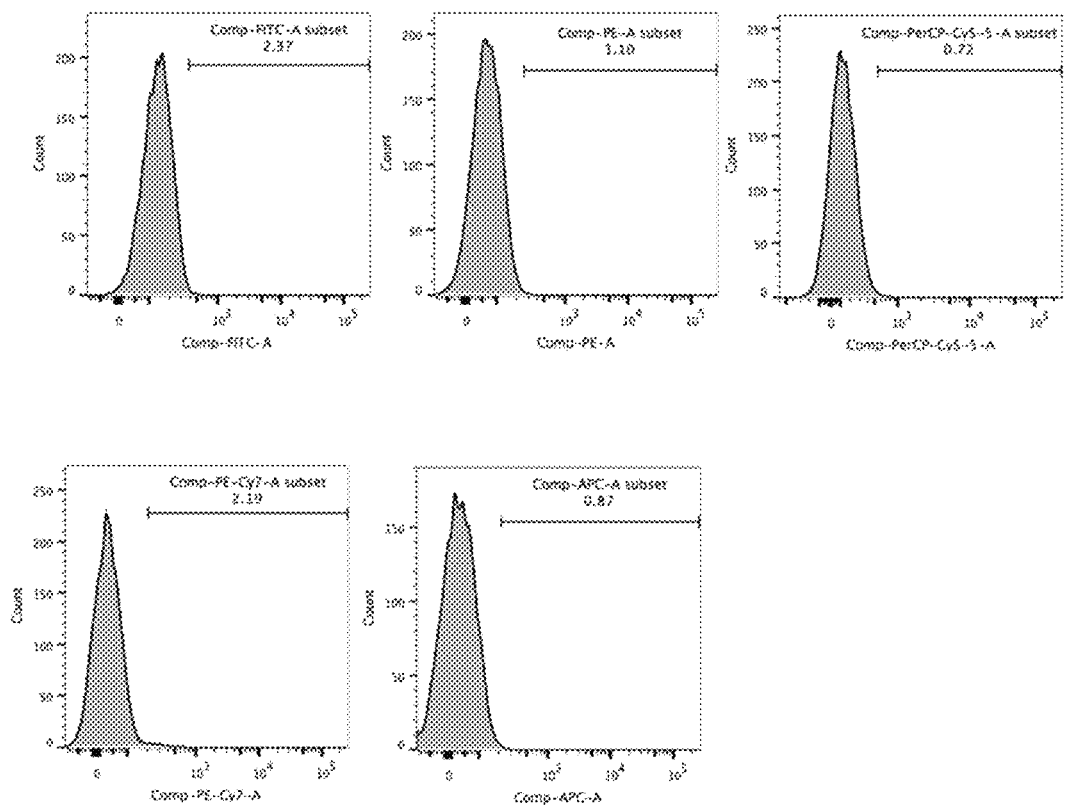

[Figure 1C]
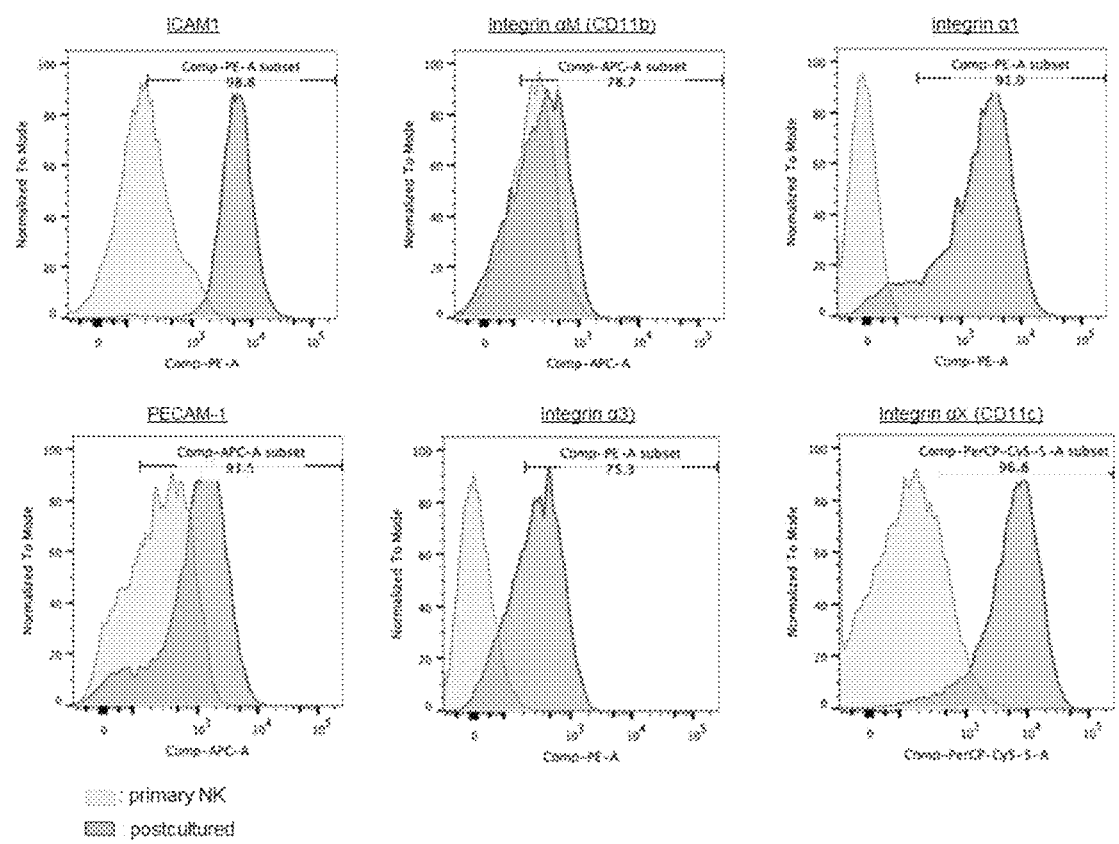

[Figure 1D]
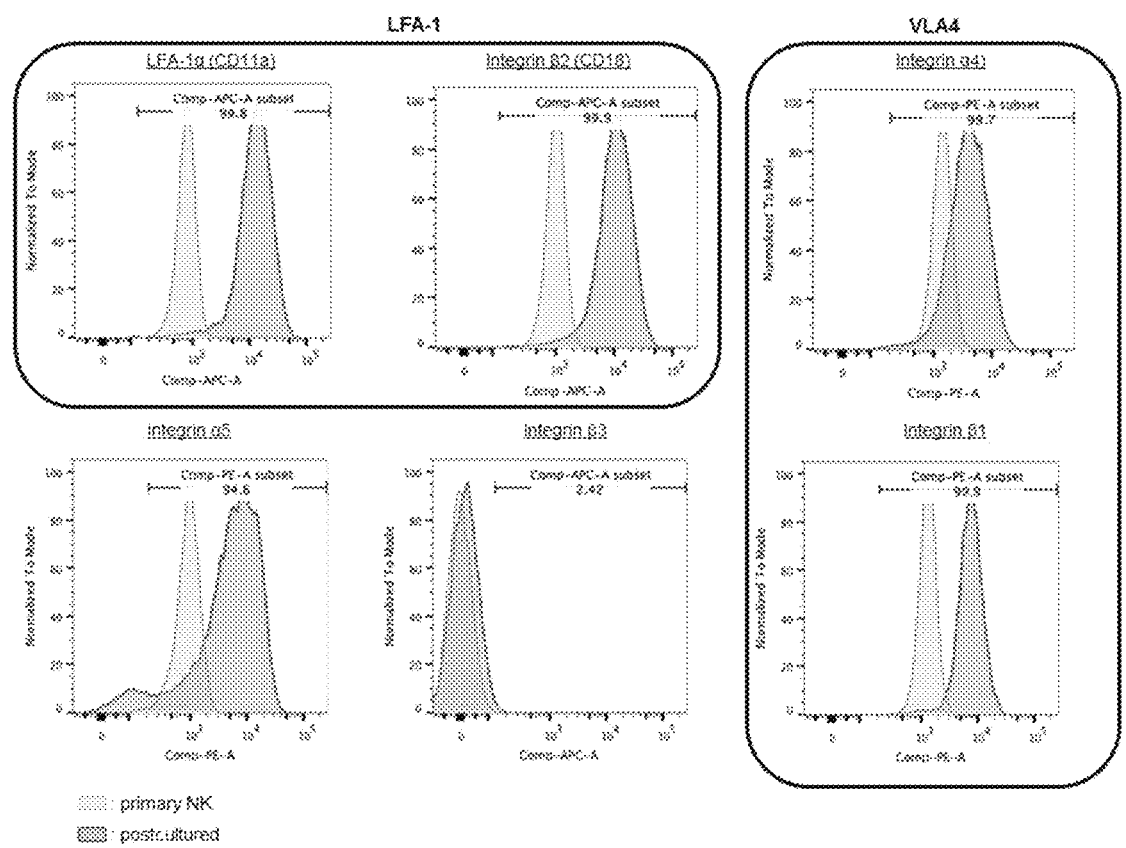

[Figure 2]
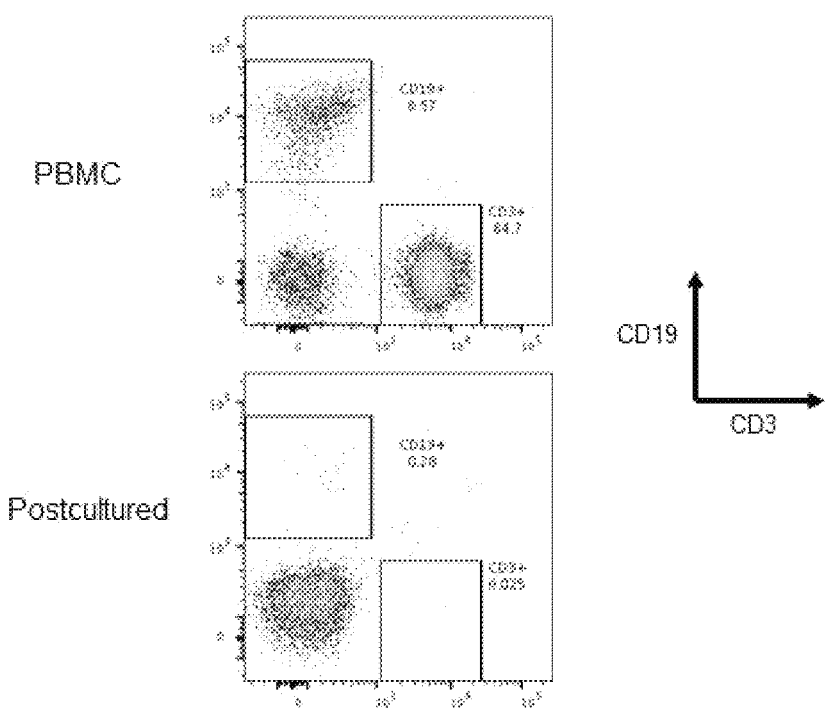
[Figure 3]
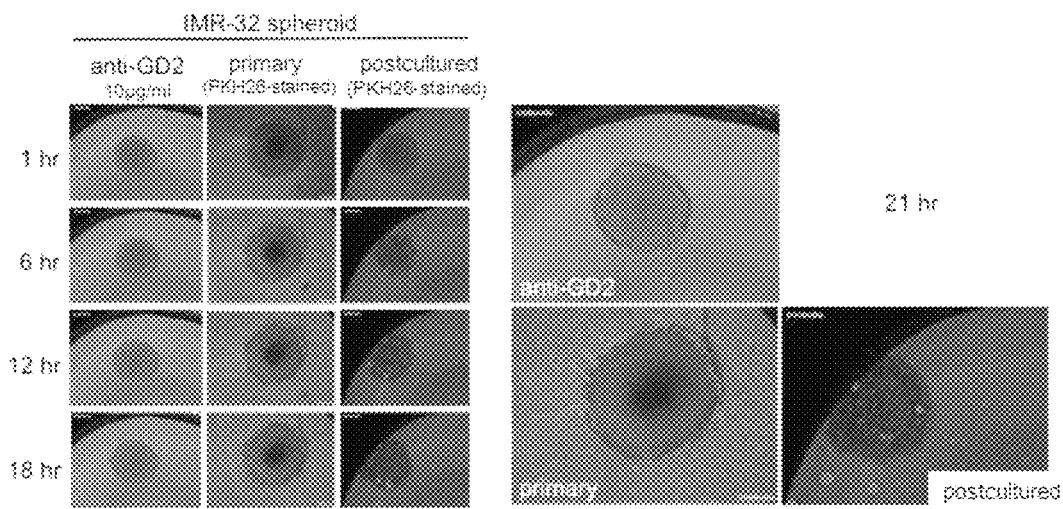

[Figure 4A]
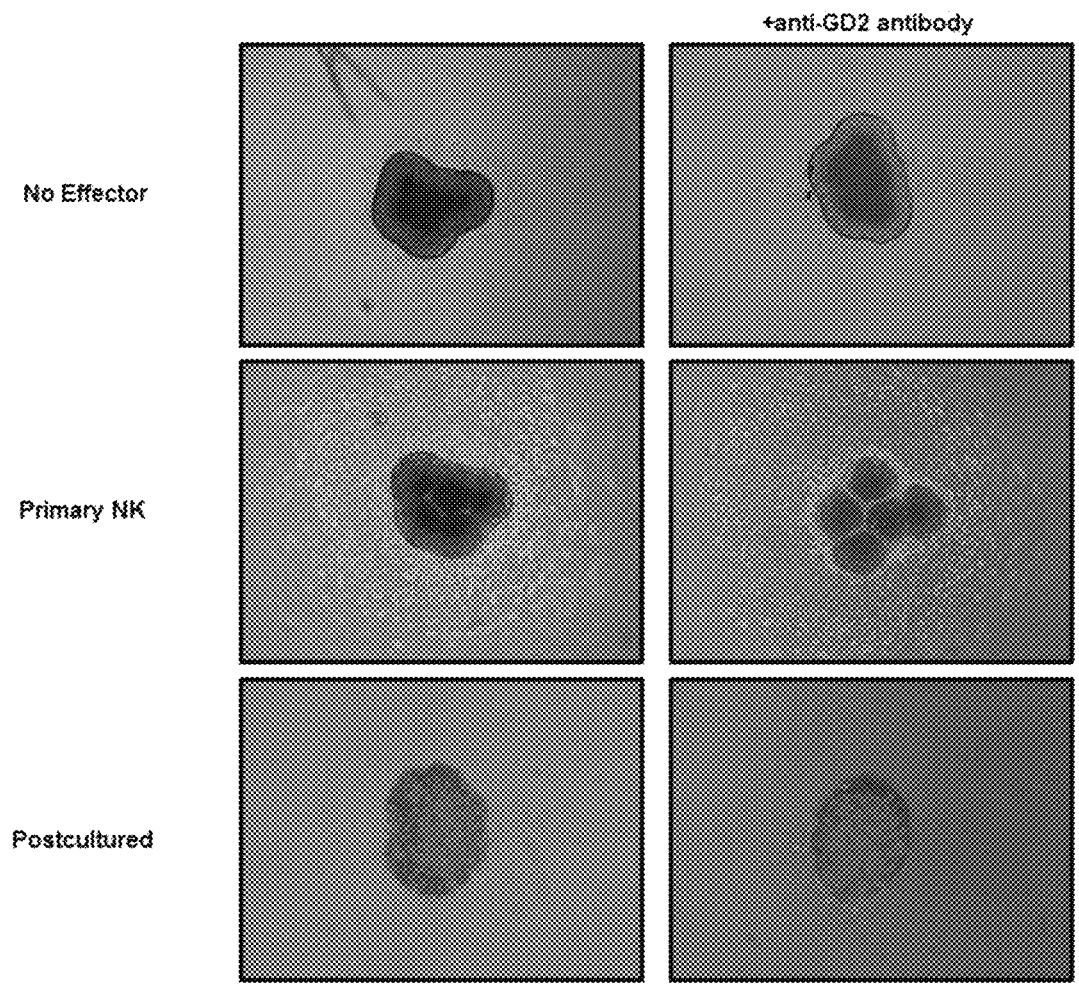

[Figure 4B]
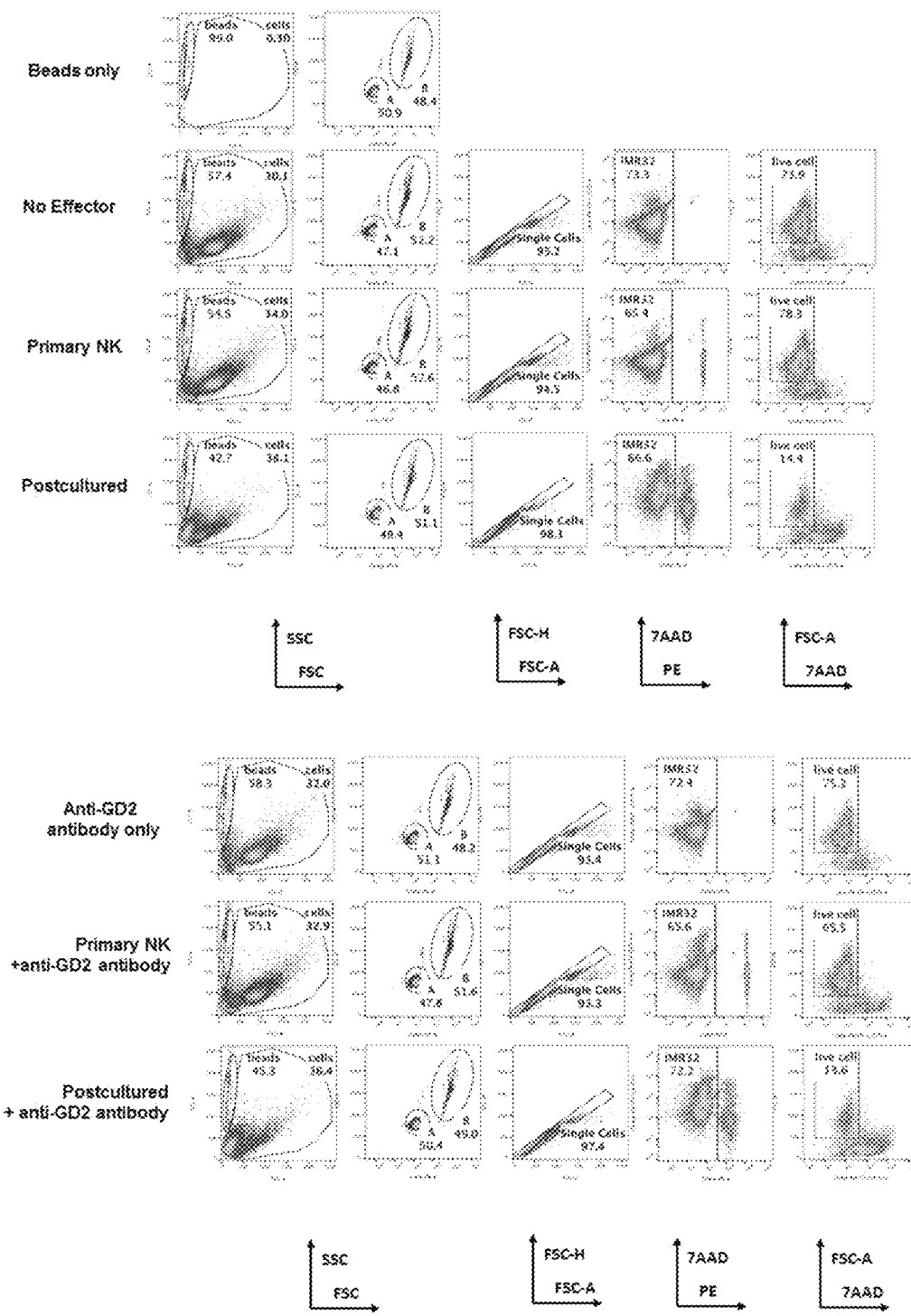

[Figure 4C]
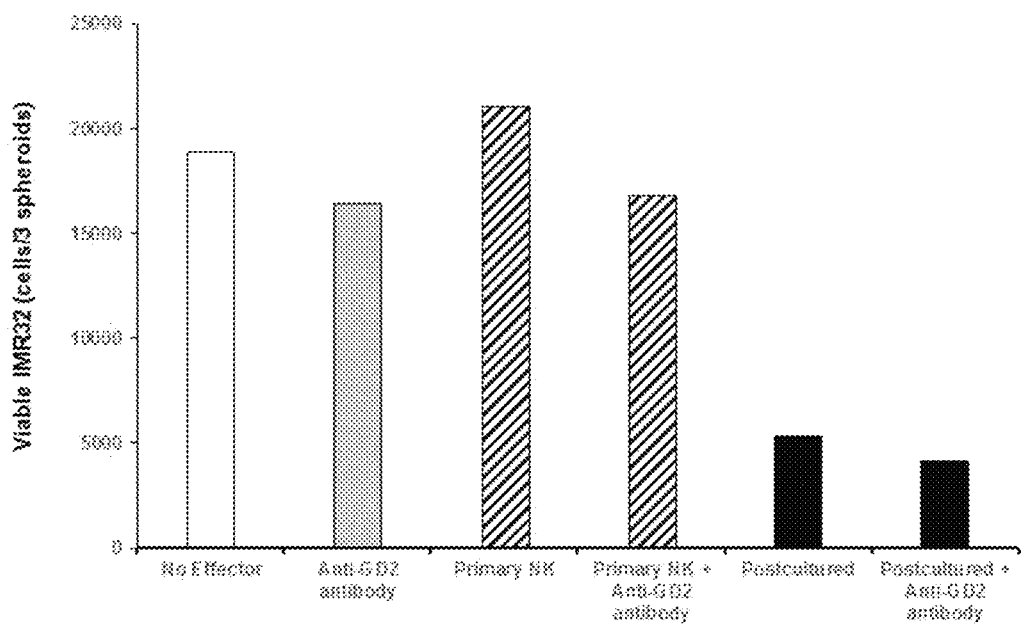
[Figure 5]
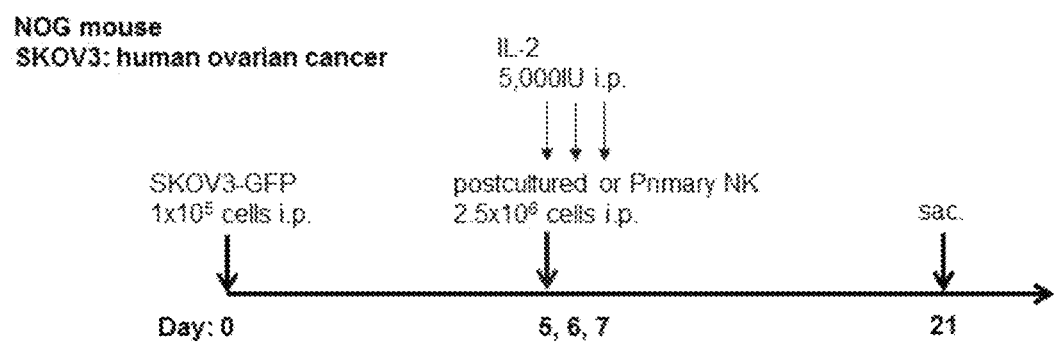

[Figure 6]
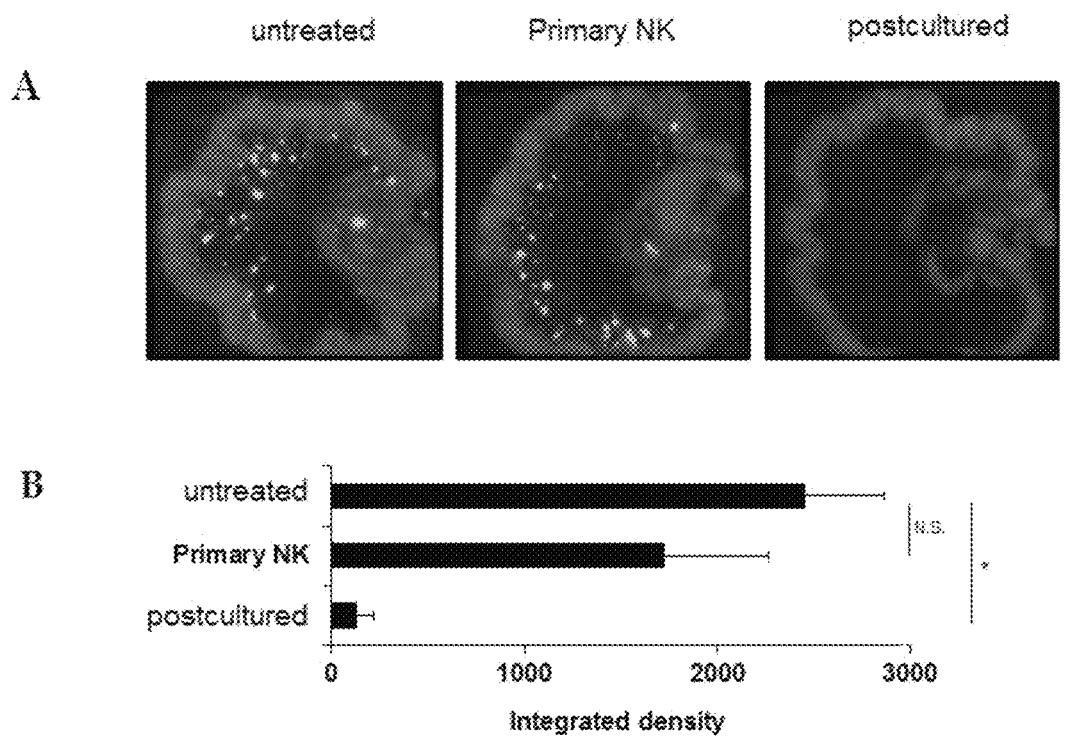
*P<0.01
One-way ANOVA, Tukey-Kramer
[Figure 7]
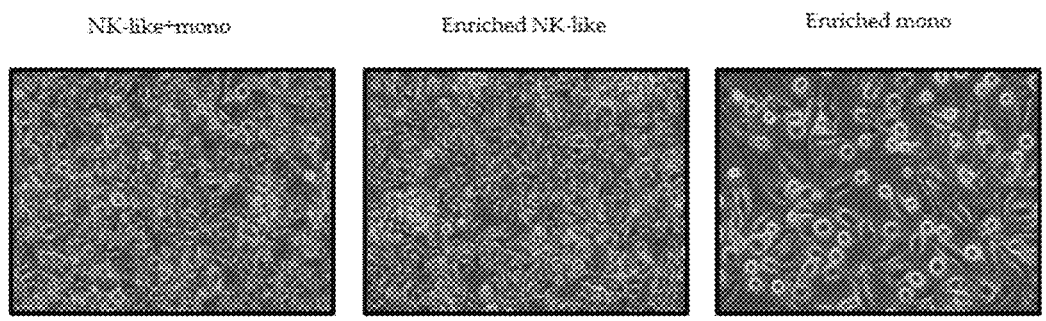

[Figure 8]
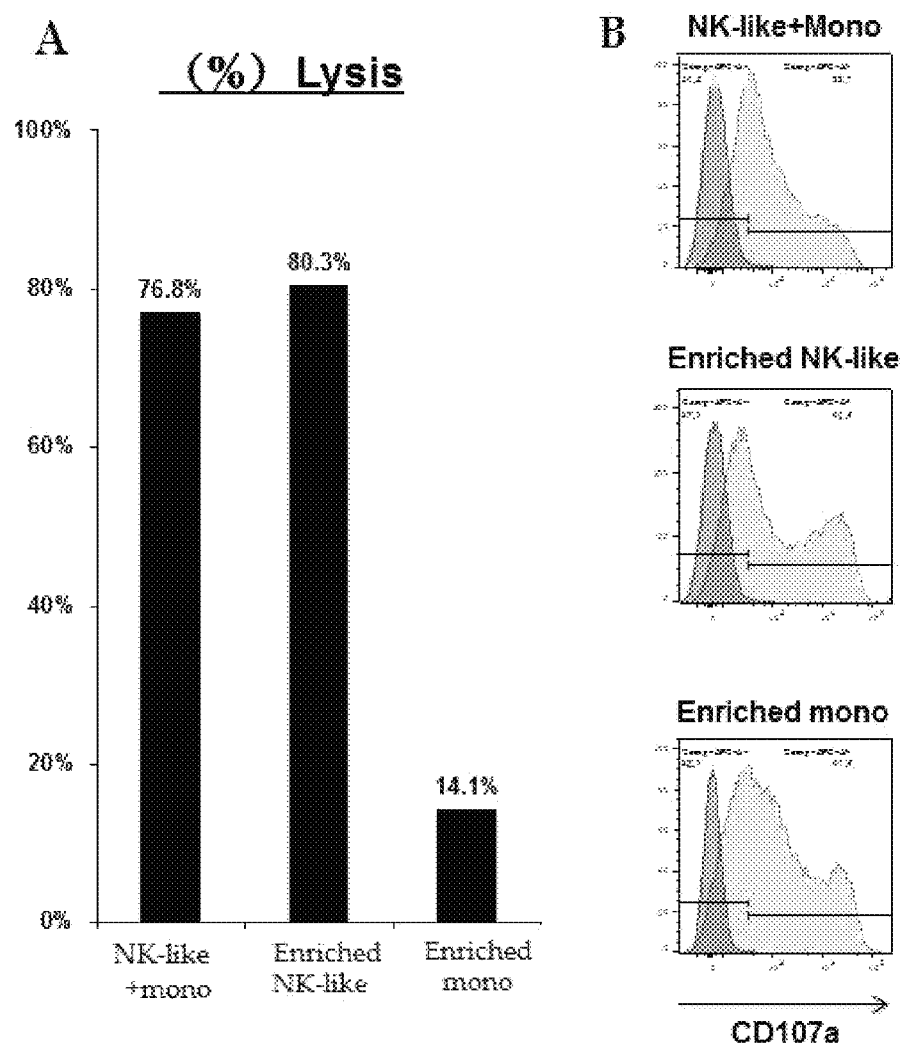

[Figure 9]
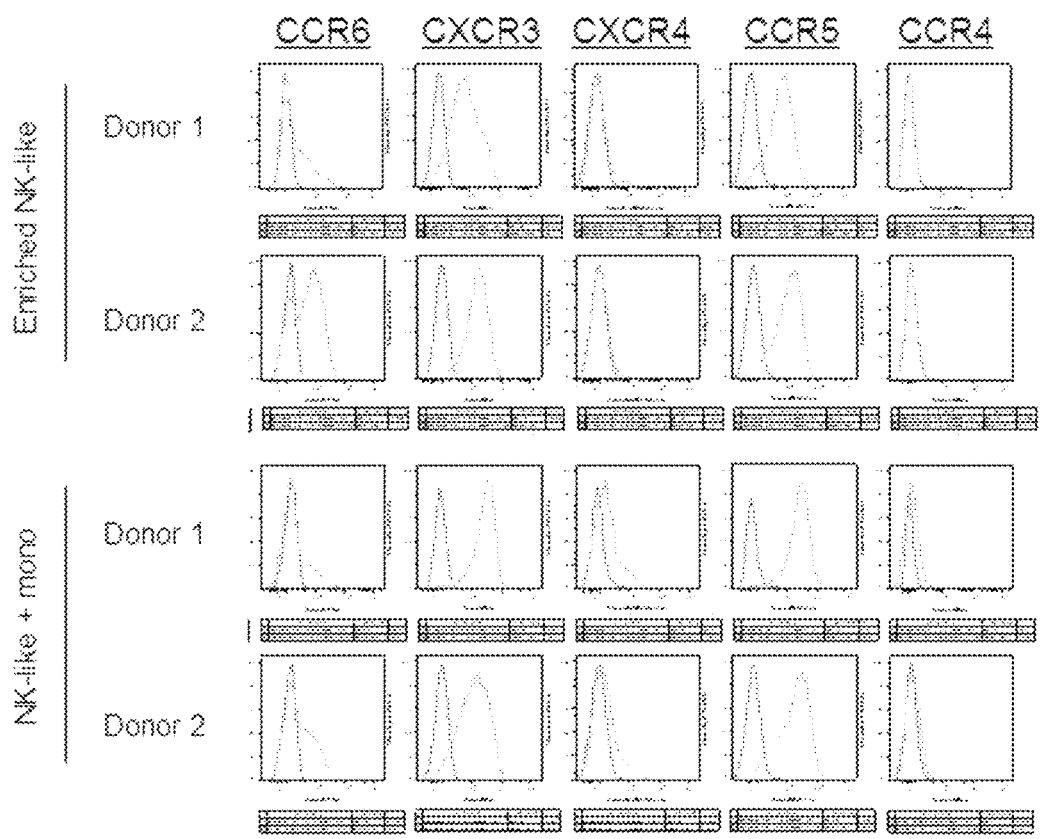

POPULATION OF CD3-NEGATIVE CELLS THAT EXPRESS CHEMOKINE RECEPTOR AND CELL ADHESION MOLECULE, USE OF THE SAME, AND METHOD FOR PRODUCING THE SAME

CROSS-REFERENCE TO RELATED APPLICATION

This application claims a convention priority based on Japanese Patent Application No. 2018-59624 filed on Mar. 27, 2018, of which entire disclosures are herein incorporated by reference.

TECHNICAL FIELD

The present invention relates to a population of CD3-negative cells that express a chemokine receptor and a cell adhesion molecule, and use of the same.

BACKGROUND ART

Natural killer cells (NK cells) are cytotoxic lymphocytes that work as a main factor of the innate immunity, and bear the responsibility of acting as an initial defense mechanism against tumor cells or virus infection.

NK cell therapies in which NK cells obtained from patients themselves are proliferated several hundreds to several thousands of times and activated by culture in the outside of the patients, and returned to the patients attract attention as therapies that give comparatively few side reactions. About $1\times10^{10}$ of mononuclear cells can usually be collected by one time of apheresis of peripheral blood of normal adult, and $7\times10^8$ of NK cells will be obtained from them if the percentage of NK cells constituting the peripheral blood mononuclear cells is supposed to be about 7%. On the other hand, if body weight of a patient is supposed to be 60 kg, it is considered that $6\times10^6$ to $4.8\times10^9$ of NK cells are required. Therefore, techniques for culturing NK cells obtained from a donor to proliferate them, and thereby obtain NK cells in an amount sufficient for annihilating target cells are being developed. For example, Patent document 1 proposes a method for proliferating NK cells, which comprises the step of preparing a cell population including NK cells, the step of removing T cells from the cell population including NK cells, and the step of culturing the cells remained after the removal of T cells in a medium containing 2500 to 2813 IU/mL of IL-2.

Although NK cells cultured ex vivo exhibit cytotoxicity against tumor cell lines in vitro, therapeutic effect thereof may not be sufficient for clinical cases. Therefore, culture techniques that increase the activity of NK cells have been proposed. For example, Patent document 2 proposes a method for ex vivo culture of NK cells, which comprises culturing a cell population including NK cells together with at least one kind of growth factor and nicotinamide and/or another nicotinamide ingredient at an effective concentration and effective exposure time for an effective period of continuing the exposure, and provides at least one of increased expression of CD62L, increased migration response, increased homing, in vivo maintenance, increased proliferation, and increased cytotoxic activity of the cells.

As immunocytes for immunocyte therapies, T cells genetically modified so that they express a chimera antigen receptor (CAR-T) are studied besides NK cells. According to a related technique, by genetically modifying T cells that do not have specificity to an antigen of a target tumor, a large amount of effector T cells that have acquired specificity to the antigen of the target tumor can be prepared from peripheral blood. However, CAR-T cell therapies may not show significant therapeutic effect for solid tumors, and as one of the causes of this, it is mentioned that the CAR-T cells do not reach a solid tumor (Non-patent document 1). As for the homing of CAR-T cells to a tumor, it has been reported that a chemokine receptor may be lost during the genetic modification, and thus migration of the cells to tumor cells may be reduced (Non-patent document 2). On the other hand, it has also been reported that migration of CAR-T cells made to express a functional chemokine receptor by transduction of CCR2b to a tumor was increased, and thus the antitumor activity thereof was increased (Non-patent document 3).

Non-patent document 4 reports an investigation of a chemokine receptor expression in the best-known CD56-positive NK cells derived from human peripheral blood. This investigation reports that major part of the $CD56^{low}$ NK cells are $CXCR1/CXCR2^+$ and $CXCR3/CCR5^{-/+}$, and most of the $CD56^{high}$ NK cells are $CXCR1/CXCR2^-$ and $CXCR3/CCR5^+$. It also reports that both $CD56^{low}$ and $CD56^{high}$ NK cells are $CCR4^-$ and $CCR6^-$ (Non-patent document 4).

Patent document 1: Japanese Patent Unexamined Publication (KOKAI) No. 2013-27385 (Japanese Patent No. 5572863)

Patent document 2: Japanese Patent Unexamined Publication (KOHYO) No. 2013-515497

Non-patent document 1: Melero I. et al., Cancer Discovery 2014; 4:522-526

Non-patent document 2: Jena B. et al., Blood, 2010; 116: 1035-1044

Non-patent document 3: Moon E. et al., Clin. Cancer Res., 2011; 17(14):4719-4730

Non-patent document 4: Lima M. et al., Journal of Immunology Research, Volume 2015, Article ID 839684, 18 pages The entire disclosures of Patent documents 1 and 2 and Non-patent documents 1 to 4 are especially incorporated herein by reference.

SUMMARY OF THE INVENTION

Object to be Achieved by the Invention

Although CAR-T cells may acquire desired functions such as chemotaxis besides the antigenic specificity through genetic manipulation, they are handled as a product for gene therapies, severe guidelines are regulated for securing quality and safety thereof, and thus they have a problem that development thereof takes much cost and time.

There is also a problem that even if it is confirmed that NK cells show cytotoxic activity against a tumor cell line in vitro, antitumor activity of the NK cells is not sufficient in vivo. It is considered that such insufficient antitumor activity is caused by the weak chemotaxis of the NK cells to tumors and no infiltration of the NK cells into solid tumors.

Although techniques for increasing efficiency of culture of NK cells and culture techniques for enhancing activities of NK cells have been so far proposed, the NK cells produced by these techniques are still insufficient for clinical use. Therefore, providing immunocytes having higher antitumor activity by using culture technique is still remain as an object to be achieved.

Means for Achieving the Object

According to the present invention, the following inventions are provided.

[1] A cell population including CCR5-positive, CCR6-positive, CXCR3-positive, and CD3-negative cells.

[2] The cell population according to [1], wherein the CCR5-positive, CCR6-positive, CXCR3-positive, and CD3-negative cells further highly express CD11a and highly express CD11c, and these highly expressing properties are judged by comparison with expressions in a population of NK cells obtained from peripheral blood and not substantially cultured.

[3] The cell population according to [1] or [2], wherein the CCR5-positive, CCR6-positive, CXCR3-positive, and CD3-negative cells are further integrin α1-positive, integrin α3-positive, and integrin β3-negative.

[4] The cell population according to any one of [1] to [3], wherein ratio of the CCR5-positive, CCR6-positive, CXCR3-positive, and CD3-negative cells is 30% or higher in the aforementioned cell population.

[5] The cell population according to any one of [1] to [4], wherein ratio of cells positive for any selected from the group consisting of CD3 and CD19 is lower than 5%.

[6] The cell population according to any one of [1] to [5], wherein cells positive for any selected from the group consisting of CD4, CD8, CD14, CD19, and CD36 have been removed from the cell population.

[7] The cell population according to any one of [1] to [6], for use in infiltration into a solid tumor.

[8] A CCR5-positive, CCR6-positive, CXCR3-positive, integrin α1-positive, integrin α3-positive, integrin β3-negative, and CD3-negative cell, which infiltrates into a solid tumor.

[9] A pharmaceutical composition, which contains the cell population according to any one of [1] to [7], and a pharmaceutically acceptable additive.

[10] A method for preparing the cell population according to any one of [1] to [7], which comprises the following steps:
preparing a primary mononuclear cell population,
removing CD3-positive cells from the primary mononuclear cell population,
removing any selected from the group consisting of monocytes and B cells from the primary mononuclear cell population, and
culturing the cell population remained after removing CD3-positive cells, and any selected from the group consisting of monocytes and B cells in a medium containing IL-2.

BRIEF DESCRIPTION OF THE DRAWINGS

FIG. 1 Expressions of chemokine receptors in cells of the present invention cultured for 14 days (postcultured). The control is primary NK cells not cultured.

FIG. 1B Negative controls using isotype control antibodies.

FIG. 1C Expressions of cell adhesion molecules in cells of the present invention cultured for 14 days (postcultured). The control is primary NK cells not cultured.

FIG. 1D Expressions of cell adhesion molecules in cells of the present invention cultured for 14 days (postcultured). The control is primary NK cells not cultured.

FIG. 2 Contents of CD3-positive cells and CD19-positive cells in cells of the present invention cultured for 14 days (postcultured). The control is PBMC.

FIG. 3 Photographs of tumor masses (IMR32 spheroids) taken at the time points of 1, 6, 12, 18 and 21 hours in a cytotoxicity assay for solid tumor mass (IMR32 spheroid) performed by using anti-GD2 antibody, primary NK cells, and cells of the present invention cultured for 14 days (postcultured).

FIG. 4A Photographs of tumor masses (IMR32 spheroids) taken at the time point of 21 hours in a cytotoxicity assay for solid tumor mass (IMR32 spheroid) performed by using primary NK cells, and cells of the present invention cultured for 14 days (postcultured). Photographs of tumor masses (IMR32 spheroids) of systems not containing effector cells are mentioned as the control.

FIG. 4B Results of flow cytometry analysis performed by using 7AAD staining for dead cells.

FIG. 4C Cytotoxic activities of primary NK and cells of the present invention cultured for 14 days (postcultured).

FIG. 5 Treatment schedule for an in vivo solid tumor model.

FIG. 6 Therapeutic effects observed in in vivo solid tumor models.
(A) Images of the whole mesenteries. The intestines are imaged in a circular shape, and the mesenteries exist in the inside thereof.
(B) The total densities of all the pixels in the GFP-positive regions of the mesenteries.

FIG. 7 Cells on the day 10 after the start of the culture according to the improved production method.

FIG. 8 (A) Cytotoxic activities of NK-like+Mono, enriched NK-like, and enriched mono. (B) CD107a-positive ratio.

FIG. 9 Verification of expressions of chemokine receptor in NK-like cells prepared by a production method using enriched NK-like cell population and NK-like+mono cell population. The curves of the enriched NK-like cells for CCR5, CCR6, and CXCR3 are indicated with arrows.

MODES FOR CARRYING OUT THE INVENTION

Although the explanations of the present invention mentioned below may be made for typical embodiments or specific examples of the present invention, the scope of the present invention is not limited to such embodiments or examples. The numerical value ranges indicated in this specification using "to" means ranges including the numerical values indicated before and behind "to" as the minimum and maximum values.

[Population of CCR5-Positive, CCR6-Positive, CXCR3-Positive, and CD3-Negative Cells]

The present invention provides a cell population including cells that are CCR5-positive, CCR6-positive, CXCR3-positive, and CD3-negative. The cells that are CCR5-positive, CCR6-positive, CXCR3-positive, and CD3-negative may be referred to as "CCR5$^+$/CCR6$^+$/CXCR3$^+$/CD3$^-$ cells" or simply as "CCR5$^+$/CCR6$^+$/CXCR3$^+$/CD3$^-$". The symbol "/" used when surface antigen markers are mentioned means "and", and for example, the expression of "CCR5$^+$/CCR6$^+$/CXCR3$^+$/CD3$^-$" means that the cells are "CCR5$^+$, CCR6$^+$, CXCR3$^+$, and CD3$^-$".

(Chemokine Receptors)

CCR5, CCR6, and CXCR3 are chemokine receptors. Chemokines and chemokine receptors are involved in cell migration in inflammation or immunological response, homing of hematopoietic stem cells to the bone marrow, and so forth. Chemokines are substances required for making leucocytes, lymphocytes, NK cells, T cells, and so forth migrate to tissues, and chemokine receptors catch the chemokines at the cell surfaces, and transmit various signals into the inside of cells.

It has been reported that CCR5 and CCR6 are contained in monocytes, macrophages, dendritic cells, and so forth, and CXCR3 is contained in T cells, NK cells, and so forth (Nagarsheth N, et al., Nat. Rev. Immunol., 2017). As for CCR5, it has been reported that it is important for the homing of cytotoxic T cells to solid tumors (Gonzaelez-Martin A, et al., Oncoimmunology, 2012). As for CCR6, it has been reported that intratumoral induction of CCR6 together with CD103 plays a role in maintenance of T cells at tumor sites (Franciszkiewicz K, et al., Cancer Res., 2012).

A population of $CCR5^+/CCR6^+/CXCR3^+/CD3^-$ cells has a characteristic of high cytotoxic activity against tumor cell lines as described later. This is a characteristic also observed for known NK cells. However, CCR6-positive NK cells have not been reported so far to date. For example, Non-patent document 4 reported that CD56-positive NK cells are CCR6-negative. Therefore, the population of $CCR5^+/CCR6^+/CXCR3^+/CD3^-$ cells provided by the present invention can be distinguished from a population of known NK cells at least in that it is CCR6-positive. The population of $CCR5^+/CCR6^+/CXCR3^+/CD3^-$ cells of the present invention may be referred to especially as a population of $CCR5^+/CCR6^+/CXCR3^+/CD3^-$ NK-like cells or simply as a population of NK-like cells. The known NK cells are large granular lymphocytes that do not express T cell receptor (TCR) and the universal T cell marker, CD3, and further do not express the B cell receptor, which is a membrane immunoglobulin, and they are usually CD16-positive in humans, even though a part of them may exist as a CD16-negative population, and are CD56-positive. Whether a certain cell is an NK cell or not can be easily determined by those skilled in the art on the basis of expression pattern of cell surface markers, or the like.

For surface markers, positivity may be represented by the symbol "+", and negativity may be represented by the symbol "−". For example, positivity for CCR5 may be represented as $CCR5^+$, negativity for CCR5 may be represented as $CCR5^-$. Positivity may mean that the cell highly expresses the marker (high), or lowly expresses the marker (low). Such positive, negative, highly expressing, and lowly expressing properties can be determined on the basis of a chart obtained by flow cytometry. Although the positions on the chart may vary depending on the setting of voltage and sensitivity in the instrument, used antibody clone, staining conditions, used dye, and so forth, those skilled in the art can appropriately classify the cells on the obtained chart without dividing a cell population that should be recognized as a single group.

Whether a cell is positive or negative for expression of a target marker can be determined by using a negative control using an isotype control antibody. The isotype control antibody is an antibody that does not react with a specific antigen. In experiments using antibodies, a background may generally be produced by nonspecific binding with a protein other than the target, or binding with the Fc receptor on the cell surfaces. By comparison with a system using an antibody that serves as a negative control, it can be clarified whether the reaction of the primary antibody with the target antigen is specific. The influence of the background is also eliminated, and therefore strength of signal can be correctly determined.

In this specification, the term "cell population" refers to a population constituted by a plurality of cells, for example, $1\times10^5$ or more of cells. The population of $CCR5^+/CCR6^+/CXCR3^+/CD3^-$ cells provided by the present invention can be prepared at various cell densities. For example, it can be prepared at a density of $1\times10^5$ cells/mL or higher.

Number of cells contained in the population of $CCR5^+/CCR6^+/CXCR3^+/CD3^-$ cells is preferably $1\times10^6$ or larger, more preferably $5\times10^6$ or larger, further preferably $1\times10^7$ or larger. The number of cells contained in the population of $CCR5^+/CCR6^+/CXCR3^+/CD3^-$ cells can be set to $1\times10^6$ to $1\times10^{10}$ as a number suitable for administration to a human. Cell density in the population of $CCR5^+/CCR6^+/CXCR3^+/CD3^-$ cells is $1\times10^5$ cells/mL or higher, preferably $2\times10^5$ cells/mL or higher, more preferably $5\times10^5$ cells/mL or higher. For drip infusion for human, the cell density can be about $5\times10^5$ cells/mL. The maximum cell density may be, for example, $1\times10^{10}$ cells/mL or lower. Although the range of the cell density in the population of $CCR5^+/CCR6^+/CXCR3^+/CD3^-$ cells is not particularly limited, it can be $1\times10^5$ to $1\times10^{10}$ cells/mL, $2\times10^5$ to $1\times10^{10}$ cells/mL, $3\times10^5$ to $1\times10^{10}$ cells/mL, $4\times10^5$ to $1\times10^{10}$ cells/mL, $5\times10^5$ to $1\times10^{10}$ cells/mL, $6\times10^5$ to $1\times10^{10}$ cells/mL, $7\times10^5$ to $1\times10^{10}$ cells/mL, $8\times10^5$ to $1\times10^{10}$ cells/mL, $9\times10^5$ to $1\times10^{10}$ cells/mL, $1\times10^6$ to $1\times10^{10}$ cells/mL, $1\times10^7$ to $1\times10^{10}$ cells/mL, $1\times10^8$ to $1\times10^{10}$ cells/mL, $1\times10^5$ to $1\times10^9$ cells/mL, $2\times10^5$ to $1\times10^9$ cells/mL, $3\times10^5$ to $1\times10^9$ cells/mL, $4\times10^5$ to $1\times10^9$ cells/mL, $5\times10^5$ to $1\times10^9$ cells/mL, $6\times10^5$ to $1\times10^9$ cells/mL, $7\times10^5$ to $1\times10^9$ cells/mL, $8\times10^5$ to $1\times10^9$ cells/mL, $9\times10^5$ to $1\times10^9$ cells/mL, $1\times10^6$ to $1\times10^8$ cells/mL, $1\times10^6$ to $1\times10^9$ cells/mL, or $1\times10^7$ to $1\times10^9$ cells/mL. The cell density in the population of $CCR5^+/CCR6^+/CXCR3^+/CD3^-$ cells can be $1\times10^6$ to $1\times10^8$ cells/mL, which is suitable for culture or cryopreservation, or $1\times10^5$ to $1\times10^9$ cells/mL, which is suitable for administration to a human.

Ratio of the CCR5-positive, CCR6-positive, CXCR3-positive, and $CD3^-$ negative cells in the cell population provided by the present invention (Ratio (%)=(Number of $CCR5^+/CCR6^+/CXCR3^+/CD3^-$ cells)/(Number of total cells) x 100) may be 30% or higher. Since it is considered that a higher ratio of CCR5-positive, CCR6-positive, CXCR3-positive, and $CD3^-$ negative cells in the aforementioned cell population provides a higher therapeutic effect, the ratio is preferably 30% or higher, 35% or higher, 40% or higher, 45% or higher, or 50% or higher. The ratio of the CCR5-positive, CCR6-positive, CXCR3-positive, and CD3-negative cells in the aforementioned cell population may be still higher, and may be 55% or higher, 60% or higher, 65% or higher, 70% or higher, 75% or higher, 80% or higher, 85% or higher, 90% or higher, or 95% or higher.

Degree of expression of a target marker (low expression or high expression) can be determined by comparison with a result of a population of control cells measured under the same conditions. An example of the population of control cells is a population of NK cells obtained from peripheral blood and not substantially cultured, such as the primary NK mentioned in the examples of this specification.

Degree of the expression of CCR6 in a cell population cultured for a certain period of time can be determined by comparing the CCR6 expression amount in the cell population with CCR6 expression amount in a population of NK cells obtained from peripheral blood and not substantially cultured (control, which is known to be CCR6-negative) by using flow cytometry. If the expression of CCR6 in the cell population cultured for a certain period of time shows bimodality, and expression amounts of the both peaks are higher than that of the control, it can be determined that there are lowly expressing cells and highly expressing cells.

The cells included in the population of $CCR5^+/CCR6^+/CXCR3^+/CD3^-$ cells provided by the present invention can highly express CCR6 or lowly express CCR6. The population of CCR5⁺/CCR6⁺/CXCR3⁺/CD3⁻ cells provided by the present invention may also include both of a population of CCR5⁺/CCR6⁺/CXCR3⁺/CD3⁻ cells that highly express CCR6, and a population of CCR5⁺/CCR6⁺/CXCR3⁺/CD3⁻ cells that lowly express CCR6. If a cell population including both of such types of populations is analyzed for CCR6 by flow cytometry, it shows bimodality.

The cells included in the population of CCR5⁺/CCR6⁺/CXCR3⁺/CD3⁻ cells provided by the present invention can also be CCR5-positive and CXCR3-positive. In addition, they may highly express CCR5 and highly express CXCR3. Whether the cells highly express them can be determined by comparison with expressions of CCR5 and CXCR3 in myelocyte type cells, such as macrophages and MDSCs.

The cells included in the population of CCR5⁺/CCR6⁺/CXCR3⁺/CD3⁻ cells provided by the present invention may be negative for any selected from the group consisting of CXCR1 and CXCR2. The cells included in the population of CCR5⁺/CCR6⁺/CXCR3⁺/CD3⁻ cells provided by the present invention may be negative for, or extremely lowly express any selected from the group consisting of CCR2, CCR4, and CXCR4.

The cell population including CCR5-positive, CCR6-positive, CXCR3-positive and CD3⁻ negative cells provided by the present invention can be obtained by the method for producing a population of NK-like cells described later. Although the method for producing a population of NK-like cells described later comprises the step of removing any selected from the group consisting of monocytes and B cells from a population of primary mononuclear cells, any selected from the group consisting of monocytes and B cells may not need to be removed.

The cells included in the cell population provided by the present invention can originate in the nature. In the present invention, the term cells that originate in the nature means that the cells are non-gene recombinant cells, cells not derived from a transgenic animal or transformant cell, or cells not created by a cell fusion technique. However, it is not meant that they are naturally existing cells themselves, but it is meant that they are cells produced by a culture technique. In the present invention, the non-gene recombinant cells means cells that have not been produced by using mononuclear cells separated from blood of an animal of which individual genetic information was artificially modified by using a genetic modification technique. Further, they do not consist of a population of cells produced from mononuclear cells or hematopoietic stem cells separated from blood by artificially modifying genetic information thereof using a genetic modification technique, either. In the present invention, the cells not derived from a transgenic animal or transformant cell mean cells produced without any step of introducing a foreign gene into an organism or cell. The term of cells not created by a cell fusion technique means that the cells are neither cells produced by cell fusion, or cells derived from such cells, and means that, for example, the cells have not been subjected to expression control for cell surface antigen by cell fusion, or the like.

(Cell Adhesion Molecule)

The CCR5⁺/CCR6⁺/CXCR3⁺/CD3⁻ cells of the cell population including CCR5-positive, CCR6-positive, CXCR3-positive and CD3-negative cells provided by the present invention can highly express CD11c (CCR5⁺/CCR6⁺/CXCR3⁺/CD3⁻/CD11c$^{high}$). CD11c is a cell adhesion molecule also known as integrin αX. It is known that CD11c is expressed in monocytes, macrophages, granulocytes, and myeloid type dendritic cells. CD11c is known to bind with CD18 and participate in cell adhesion, and so forth.

Degree of the expression of CD11c in a cell population cultured for a certain period of time can be determined by comparing the CD11c expression amount in the cell population with CD11c expression amount in a population of NK cells obtained from peripheral blood and not substantially cultured (control, which is known to lowly express CD11c) by using flow cytometry. If the expression of CD11c in the cell population cultured for a certain period of time is higher than that of the control, it can be determined that the cells highly express CD11c.

The CCR5⁺/CCR6⁺/CXCR3⁺/CD3⁻ cells of the cell population including CCR5-positive, CCR6-positive, CXCR3-positive and CD3-negative cells provided by the present invention can highly express CD11a/CD18 (CCR5⁺/CCR6⁺/CXCR3⁺/CD3⁻/CD11a$^{high}$, and CCR5⁺/CCR6⁺/CXCR3⁺/CD3⁻/CD18$^{high}$). $^{CD}$11a/CD18 are also called LFA-1 as a synonym, and they are known to be distributed in T lymphocytes, and participate in adhesion and chemotaxis of leucocytes through interactions with ICAM-1 or ICAM-4 to induce immunological tolerance.

Degree of the expression of CD11a/CD18 in a cell population cultured for a certain period of time can be determined by comparing the CD11a/CD18 expression amount in the cell population with CD11a/CD18 expression amount in a population of NK cells obtained from peripheral blood and not substantially cultured (control, which is known to lowly express CD11a/CD18) by using flow cytometry. If the expression of CD11a/CD18 in the cell population cultured for a certain period of time is higher than that of the control, it can be determined that the cell population highly expresses CD11a/CD18.

The CCR5⁺/CCR6⁺/CXCR3⁺/CD3⁻ cells of the cell population including CCR5-positive, CCR6-positive, CXCR3-positive and CD3-negative cells provided by the present invention further can highly express any selected from the group consisting of integrin α1, integrin α3, integrin α4, integrin α5, ICAM-1, and integrin β1. Whether the cells highly express them can be determined by comparison with expressions of them in a population of NK cells obtained from peripheral blood and not substantially cultured (control, known to be negative for, or lowly express integrin α1, integrin α3, integrin α4, integrin α5, ICAM-1, and integrin β1).

Integrin α4/integrin β1 are called VLA-4 as a synonym, and are known to participate in migration of lymphocytes, monocytes, and eosinophiles to inflammation sites through interactions with fibronectin, VCAM-1, and so forth. Integrin α1/integrin β1 are called VLA-1 as a synonym, and are known to be distributed in an extensive range of cells, and participate in neural spine extension or lymphocytic infiltration through interactions with collagen and laminin. Integrin α3/integrin β1 are called VLA-3 as a synonym, and are known to be distributed over an extensive range of cells, and participate in morphogenesis of the kidney or lung, and infiltration and metastasis of cancer through interactions with laminin 5, TSP, and uPAR.

In the cell population provided by the present invention including CCR5-positive, CCR6-positive, CXCR3-positive, and CD3-negative cells, the CCR5-positive, CCR6-positive, CXCR3-positive, and CD3-negative cells can further be integrin α1-positive, integrin α3-positive, and integrin β3-negative. As shown in FIGS. 1C and 1D mentioned in Example 1 described later, NK cells before being cultured (primary NK) are negative for all of integrins α1, α3 and β3.

On the other hand, NK cells after being cultured for two weeks are known to be positive for all of integrins α1, α3 and β3 (Maenpaa et al., Int. J. Cancer, 53, 850-855, 1993, Tables II, III, FIG. 2). The CCR5-positive, CCR6-positive, CXCR3-positive and CD3-negative cells included in the cell population provided by the present invention are different from culture of conventional NK cells at least in that they are integrin α1-positive, integrin α3-positive, and integrin β3-negative.

The CCR5$^+$/CCR6$^+$/CXCR3$^+$/CD3$^-$ cells of the cell population including CCR5-positive, CCR6-positive, CXCR3-positive and CD3-negative cells provided by the present invention may highly express integrin α4/integrin β1. The CCR5$^+$/CCR6$^+$/CXCR3$^+$/CD3$^-$ cells of the cell population including CCR5-positive, CCR6-positive, CXCR3-positive and CD3-negative cells provided by the present invention may highly express integrin α1/integrin β1. The CCR5$^+$/CCR6$^+$/CXCR3$^+$/CD3$^-$ cells of the cell population including CCR5-positive, CCR6-positive, CXCR3-positive and CD3-negative cells provided by the present invention may highly express integrin α3/integrin β1.

The population of NK-like cells provided by the present invention may be a population of CCR5$^+$/CCR6$^+$/CXCR3$^+$/CD3$^-$, CCR5$^+$/CCR6$^+$/CXCR3$^+$/CD3$^{31}$/CD11c$^{high}$, CCR5$^+$/CCR6$^+$/CXCR3$^+$/CD3$^-$/CD11c$^{high}$/CD11a$^{high}$, CCR5$^+$/CCR6$^+$/CXCR3$^+$/CD3$^-$/CD11c$^{high}$/CD11a$^{high}$/CD18$^{high}$, CCR5$^+$/CCR6$^+$/CXCR3$^+$/CD3$^-$/CD11c$^{high}$/CD11a$^{high}$/CD18$^{high}$/integrin α1$^{high}$, CCR5$^+$/CCR6$^+$/CXCR3$^+$/CD3$^-$/CD11c$^{high}$/CD11a$^{high}$/CD18$^{high}$/integrin α1$^{high}$/integrin α3$^{high}$, CCR5$^+$/CCR6$^+$/CXCR3$^+$/CD3$^-$/CD11c$^{high}$/CD11a$^{high}$/CD18$^{high}$/integrin α1$^{high}$/integrin α3$^{high}$/integrin α4$^{high}$, CCR5$^+$/CCR6$^+$/CXCR3$^+$/CD3$^-$/CD11c$^{high}$/CD11a$^{high}$/CD18$^{high}$/integrin α1$^{high}$/integrin α3$^{high}$/integrin α4$^{high}$/integrin α5$^{high}$, CCR5$^+$/CCR6$^+$/CXCR3$^+$/CD3$^-$/CD11c$^{high}$/CD11a$^{high}$/CD18$^{high}$/integrin α1$^{high}$/integrin α3$^{high}$/integrin α4$^{high}$/integrin α5$^{high}$/ICAM-1$^{high}$, or CCR5$^+$/CCR6$^+$/CXCR3$^+$/CD3$^-$/CD11c$^{high}$/CD11a$^{high}$/CD18$^{high}$/integrin α1$^{high}$/integrin α3$^{high}$/integrin α4$^{high}$/integrin α5$^{high}$/ICAM-1$^{high}$/integrin β1$^{high}$, or CCR5$^+$/CCR6$^+$/CXCR3$^+$/CD3$^-$/integrin α1$^{high}$, CCR5$^+$/CCR6$^+$/CXCR3$^+$/CD3$^-$/integrin α1$^{high}$/integrin α3$^{high}$, CCR5$^+$/CCR6$^+$/CXCR3$^+$/CD3$^-$/integrin α1$^{high}$/integrin α3$^{high}$/integrin α4$^{high}$, CCR5$^+$/CCR6$^+$/CXCR3$^+$/CD3$^-$/integrin a1$^{high}$/integrin α3$^{high}$/integrin α4$^{high}$/integrin α5$^{high}$, CCR5$^+$/CCR6$^+$/CXCR3$^+$/CD3$^-$/integrin α1$^{high}$/integrin α3$^{high}$/integrin α4$^{high}$/integrin α5high/ICAM-1$^{high}$, or CCR5$^+$/CCR6$^+$/CXCR3$^+$/CD3$^-$/integrin α1$^{high}$/integrin α3$^{high}$/integrin α4$^{high}$/integrin a5$^{high}$/ICAM-1$^{high}$/integrin β1$^{high}$ cells.

The aforementioned specific NK-like cells included in the population of NK-like cells provided by the present invention may be positive for any selected from the group consisting of CD16 and CD56 or both of them. For example, the CCR5$^+$/CCR6$^+$/CXCR3$^+$/CD3$^-$ cells included in the population of CCR5$^+$/CCR6$^+$/CXCR3$^+$/CD3$^-$ cells provided by the present invention may be positive for any selected from the group consisting of CD16 and CD56 or both of them. The aforementioned specific NK-like cells included in the population of NK-like cells provided by the present invention may be negative for any selected from the group consisting of CXCR1 and CXCR4 or both of them.

Ratio of cells that are positive for any selected from the group consisting of CD3 and CD19 in the population of NK-like cells provided by the present invention can be lower than 10%. The ratio of these cells in the cell population can be analyzed by flow cytometry. The ratio of cells that are positive for any selected from the group consisting of CD3 and CD19 in the cell population is preferably lower than 5%, more preferably lower than 2%. This is because it is considered that a higher ratio of the CCR5-positive, CCR6-positive, CXCR3-positive, and CD3-negative cells in the cell population provides higher tumor cytotoxic activity.

(Chemotaxis and Infiltration)

The population of NK-like cells provided by the present invention may show increased chemotaxis to tumor sites. The population of NK-like cells provided by the present invention can infiltrate into a tumor mass. Infiltration into a tumor mass means a state that cells (for example, immunocytes) are invading into inside of a tumor mass.

Chemotaxis to a tumor site can be evaluated by cell migration assay. Cell migration assay can be carried out in the presence of tumor cells by the transwell method, or the like.

The population of NK-like cells provided by the present invention can show increased chemotaxis to a tumor site compared with a population of NK cells obtained from peripheral blood and not substantially cultured. According to the study of the inventors of the present invention, it is considered that higher expressions of chemokine receptors CCR5, CXCR3, and CCR6 in the population of NK-like cells provided by the present invention compared with a population of NK cells obtained from peripheral blood and not substantially cultured relate to the increased chemotaxis to a tumor site.

Infiltration into a tumor mass can be evaluated by a cytotoxicity assay for spheroid created from a tumor cell line. Spheroid is a three-dimensional cell cultured aggregated cell mass, in which interactions among cells and extracellular matrixes are developed. Tight junctions may exist in a peripheral part thereof, and it is considered that metabolisms and functional activities in the inside thereof are closer to those of living bodies, because of hypoxic condition and low pH. Tumor spheroids are expected as a next generation in vitro experimental model for drug development (Hirschhaeuser F. et al., J. Biotechnol., 2010 Jul. 1; 148(1):3-15; Xiang X. et al., 2011 PLoS ONE 6(1):e14640. doi:10.1371/journal.pone.0014640; Milotti E., Chignola R., 2010 PLoS ONE 5(11):e13942. doi:10.1371/journal.pone.0013942). For example, the NK-like cells provided by the present invention can be labeled with fluorescence, and migration thereof into the inside of spheroid can be observed. Although NK cells obtained from peripheral blood and not substantially cultured do not infiltrate into spheroid, the NK-like cells provided by the present invention can infiltrate into spheroid. It is considered that the cell adhesion molecules LFA-1/VLA-4 are important for infiltration into a solid tumor (Sackstein R., et al., Lab. Invest., 2017). According to the study of the inventors of the present invention, it is considered that higher expressions of cell adhesion molecules in the population of NK-like cells provided by the present invention compared with a population of NK cells obtained from peripheral blood and not substantially cultured relate to infiltration into spheroids.

In a cytotoxicity assay using a spheroid formed from the IMR32 cell line (human MYCN-amplified neuroblastoma cell line) as a solid tumor mass, NK cells obtained from peripheral blood and not substantially cultured existed around the spheroid, but they did not show infiltration. Further, it is considered that anti-GD2 antibody (Unituxin (registered trademark)) can injure the IMR32 cell line by itself (Doronin et al., BMC Cancer, 2014, 14:295), but such a morphological change as is provided by cytotoxicity was not microscopically observed for IMR32 cells forming the spheroid. On the other hand, the population of CCR5$^+$/CCR6$^+$/CXCR3$^+$/CD3$^-$ cells provided by the present invention infiltrated into the spheroid, and the spheroid began to collapse after 12 hours from the start of the assay.

In addition, the cytotoxic activity of the population of NK-like cells provided by the present invention against the spheroid was extremely higher than that of the NK cells obtained from peripheral blood and not substantially cultured. Further, there was no significant difference of cytotoxic activity against the spheroid between the system using the population of NK-like cells provided by the present invention and antibody together, and the system not using the antibody together.

As described above, the population of NK-like cells provided by the present invention can show high cytotoxic activity. The cytotoxic activity refers to an ability of a subject cell (effector cell, E) to lyse a target cell (T), unless especially indicated. The cytotoxic activity can be represented by a percentage (%) of the target cells killed by the effector cells, and obtained in accordance with the following equation. (Cell death found in co-culture with effector cells−Natural cell death (negative control))/(Maximum cell death (positive control)−Natural cell death (negative control))×100

When cytotoxic activity of the NK-like cells provided by the present invention as the effector cells against a solid tumor mass is measured, spheroids of IMR32 cell line as well as spheroids created from tumor cell lines of glioma, breast cancer, large intestine cancer, ovarian cancer, prostate cancer, and so forth can be used as the target cells, but the target cells are not limited to these. Although size of the usable spheroid can be about 150 to 500 μm in diameter, the size is not limited to be in such a range. The effector cells and target cells, and live cells and dead cells can be distinguished and quantified by using a reagent such as antibody labeled with a radioactive substance, fluorescent dye, or the like. The cytotoxic activity of NK-like cells used as the effector cells can be measured by, for example, using spheroids of IMR32 cell line as the target under the conditions of incubation time of 8 to 48 hours, preferably 12 to 24 hours.

The present invention provides a CCR5-positive, CCR6-positive, CXCR3-positive, and CD3-negative cell that infiltrates into a solid tumor. Although it is considered that the conventional NK cells are not effective for a solid tumor, the population of the CCR5$^+$/CCR6$^+$/CXCR3$^+$/CD3$^-$ cells provided by the present invention can infiltrate into a solid tumor, and injure the tumor cells. Infiltration of the CCR5$^+$/CCR6$^+$/CXCR3$^+$/CD3$^-$ cells into a solid tumor can be determined by observation of migration of the cells into the inside of the tumor mass (spheroid), morphological change of tumor mass over time, and collapse of the tumor mass. Injury of the tumor cells can be confirmed by increase in number of dead cells measured by flow cytometry.

(In Vivo Therapeutic Effect for Solid Tumor)

The population of CCR5$^+$/CCR6$^+$/CXCR3$^+$/CD3$^-$ NK-like cells provided by the present invention can show a therapeutic effect for a solid tumor in vivo.

The in vivo therapeutic effect for a solid tumor can be evaluated by transplanting human tumor cells to an animal such as an immunodeficient mouse, and observing progress thereof. Prophylactic effect of the population of NK-like cells can be evaluated by administering it simultaneously with the transplantation. The therapeutic effect can also be evaluated by confirming growth of tumor for about 5 days, and then administering the population of the NK-like cells. The evaluation can be performed by dissecting euthanized mice and observing the tumor cells labeled with fluorescence.

As for in vivo treatment scheme, the cells may be administered to an animal by a single administration or two or more times of administration. Regardless of whether the cells are administered by an independent single administration or continuous injection, initial candidate dose of the population of NK-like cells is $1\times10^5$ to $1\times10^8$ cells per kg. IL-2 can be administered together with the population of NK-like cells. IL-2 can be administered in order to maintain the activity of the administered NK-like cells in the animal. Initial candidate dose of IL-2 is 1,000 to 10,000 IU per animal. For in vivo treatment scheme, intramuscular, intravenous, intraarterial, intraperitoneal, or subcutaneous administration by an arbitrary appropriate means can be used. The therapeutic effect can be evaluated by observing fluorescence-labeled tumor cells, and/or calculating number of pixels of a fluorescence-positive region.

The population of NK-like cells provided by the present invention can decrease number of SKOV3 cells (human ovarian cancer cell line) transplanted to an immunodeficient mouse more compared with the population of NK cells obtained from peripheral blood and not substantially cultured. The population of NK-like cells provided by the present invention can substantially extinguish SKOV3 cells (human ovarian cancer cell line) transplanted to an immunodeficient mouse. It was confirmed that SKOV3 cells transplanted to an immunodeficient mouse formed tumor nodes when the mouse was not treated at all, but in a mouse treated with the population of NK-like cells provided by the present invention, SKOV3 cells substantially disappeared, and tumor nodes were not observed. On the basis of the infiltrating ability to a tumor mass observed in vitro, and the results for the in vivo therapeutic effect, it can be said that the population of CCR5$^+$/CCR6$^+$/CXCR3$^+$/CD3$^-$ NK-like cells provided by the present invention can infiltrate into a solid tumor, and injure tumor cells.

[Method for Producing Population of NK-Like Cells]

The present invention provides a method for producing a population of CCR5-positive, CCR6-positive, CXCR3-positive, and CD3-negative cells, which comprises the step of preparing a primary mononuclear cell population, the step of removing CD3-positive cells from the primary mononuclear cell population, the step of removing any selected from the group consisting of monocytes and B cells from the primary mononuclear cell population, and the step of culturing the cell population remained after removing CD3-positive cells, and any selected from the group consisting of monocytes and B cells in a medium containing IL-2.

(Primary Mononuclear Cell Population)

In the production method of the present invention, the primary mononuclear cell population can be obtained by the step of separating mononuclear cells from hemocyte cells extracted from a test subject. The hemocyte cells may be extracted from any selected from the group consisting of peripheral blood, cord blood, bone marrow, and lymph gland. The hemocyte cells may be extracted from peripheral blood by the apheresis method. The primary mononuclear cell population may not include CCR5$^+$/CCR6$^+$/CXCR3$^+$/CD3$^-$ cells before culture.

In the production method of the present invention, the primary mononuclear cell population may be prepared from at least one kind of cells selected from the group consisting of hematopoietic stem cells derived from stem cells selected from the group consisting of embryonic stem cells, adult stem cells, and induced pluripotent stem (iPS) cells, hematopoietic stem cells derived from cord blood, hematopoietic stem cells derived from peripheral blood, hematopoietic stem cells derived from bone marrow blood, cord blood mononuclear cells, and peripheral blood mononuclear cells. The test subject, who is the donor of the primary mononuclear cell population, may be a patient himself or herself who is the recipient, a close relative of the patient, or a person who has not any blood relationship with the patient. The test subject may be a healthy subject or a patient suffering from a disease. The NK-like cells provided by the present invention may be derived from a donor whose major histocompatibility antigen (MHC) and killer immunoglobulin-like receptor (KIR) do not agree with those of the recipient.

(Removal of CD3-Positive Cells and Removal of Any Selected from the Group Consisting of Monocytes and B Cells)

In the production method of the present invention, T cells and/or NKT cells may be removed by the step of removing CD3-positive cells from the primary mononuclear cell population. The removal of T cells may be attained by the step of removing, besides CD3-positive cells, one or two kinds selected from CD4-positive cells and CD8-positive cells. As for the step of removing any selected from the group consisting of monocytes and B cells from the primary mononuclear cell population in the production method of the present invention, the removal of monocytes may be attained by the step of removing one, two, or three kinds of cells selected from CD14-positive cells, CD36-positive cells, and HLA-DR-positive cells. The removal of B cells may be attained by the step of removing one or two kinds of cells selected from CD19-positive cells and CD20-positive cells.

In the production method of the present invention, the removal of CD3-positive cells and the removal of any selected from the group consisting of monocytes and B cells may be performed simultaneously, or may be performed as separate steps. The removal of monocytes and the removal of B cells may be performed simultaneously, or may be performed as separate steps.

The method for producing NK-like cells of the present invention may comprise the step of removing any selected from the group consisting of dendritic cells, granulocytes, and macrophages from the primary mononuclear cell population. The removal of any selected from the group consisting of dendritic cells, granulocytes, and macrophages may be performed by the step of removing one, two, or three kinds of cells selected from CD66b-positive cells, CD123-positive cells, and HLA-DR-positive cells.

The method for producing NK-like cells of the present invention may comprise the step of removing hematopoietic precursor cells from the primary mononuclear cell population. The step of removing hematopoietic precursor cells may be attained by the step of removing CD34-positive cells.

The method for producing NK-like cells of the present invention may comprise the step of removing erythrocytes and erythroblastic precursor cells from the primary mononuclear cell population. The step of removing erythrocytes and erythroblastic precursor cells may be attained by the step of removing glycophorin A-positive cells.

The primary mononuclear cell population can be prepared by using any of various procedures known to those skilled in the art. For example, when mononuclear cells are collected from blood such as cord blood and peripheral blood, specific gravity centrifugation can be used. Further, the primary mononuclear cell population, and the cell population remained after the removal of CD3-positive cells and removal of any selected from the group consisting of monocytes and B cells from the primary mononuclear cell population can be immunofluorescently stained with an antibody specific to a cell surface marker, then isolated and identified by using a cell sorter or flow cytometer. Further, the cell population remained after the removal of CD3-positive cells and the removal of any selected from the group consisting of monocytes and B cells from the primary mononuclear cell population may also be prepared by separating and removing cells expressing a specific cell surface antigen using magnetic beads such as, but not limited to, Dynabeads (trademark) produced by Dynal Biotech and sold by Invitrogen, and CliniMACS (trademark) of Miltenyi Biotec.

By using a specific binding partner for T cells, NKT cells, monocytes, B cells, dendritic cells, granulocytes, macrophages, erythrocytes, erythroblastic precursor cells, or hematopoietic precursor cells, T cells, NKT cells, monocytes, B cells, dendritic cells, granulocytes, macrophages, erythrocytes, erythroblastic precursor cells, or hematopoietic precursor cells may be selectively injured or killed.

The step of removing CD3-positive cells from the primary mononuclear cell population, and the step of removing any selected from the group consisting of monocytes and B cells from the primary mononuclear cell population may be the step of removing CD3-positive cells, monocytes, and B cells. The step of removing CD3-positive cells, monocytes, and B cells may be the step of removing cells of another type, such as any selected from the group consisting of erythrocytes, erythroblastic precursor cells, hematopoietic precursor cells, dendritic cells, granulocytes, macrophages, and NKT cells, together with CD3-positive cells, monocytes, and B cells.

(Medium)

The cell culture medium used for culturing a cell population remained after the removal of CD3-positive cells and removal of any selected from the group consisting of monocytes and B cells from the primary mononuclear cell population may be the KBM501 medium (Kohjin Bio, containing 1,750 JRU/ml of IL-2, for primary culture of human NK cells), CellGro SCGM medium (CellGenix, sold by Iwai Chemicals), X-VIVO15 medium (Lonza, sold by Takara Bio), Cosmedium 008 (Cosmo Bio, containing 1,750 JRU/ml of IL-2, for primary culture of human NK cells), CTS AIM V Medium, Gibco™ CTS™ AIM V™ Medium (Thermo Fisher Scientific, serum-free medium of known composition for proliferating and manipulating T cells and dendritic cells), CTS OpTmizer T Cell Expansion Basal Medium (Thermo Fisher Scientific, for growing and proliferating human T lymphocytes), IMDM, MEM, DMEM, RPMI-1640, or the like, but it is not limited to these.

The medium may contain interleukin-2 (IL-2) at such a concentration that the object of the present invention can be achieved. The concentration of IL-2 may be 100 to 5000 IU/mL. The concentration of IL-2 may also be 2500 to 2813 IU/mL. IL-2 preferably has the amino acid sequence of human IL-2, and it is preferably prepared by a recombinant DNA technique in view of safety. The concentration of IL-2 may be represented with the Japanese reference unit (JRU) or international unit (IU). 1 IU corresponds to about 0.622 JRU.

The medium may contain autoserum of the test subject, human AB type serum available from BioWhittaker or the like, or donated human blood serum albumin available from the Japanese Red Cross Society. Autoserum and human AB type serum are preferably added at a concentration of 1 to 10%, and donated human blood serum albumin is preferably added at a concentration of 1 to 10%. Although the serum contained in the medium may be human serum or nonhuman animal serum, it is preferably human serum albumin. Instead of the serum, a platelet extract available from Corefront Corporation or the like (UltraGro™ etc.) can be used. The platelet extract is preferably added at a concentration of 1 to 10%, The medium may contain an appropriate protein, cytokine, antibody, compound, and other ingredients on condition that the amplification effect for NK-like cells is not impaired. The cytokine may be selected from the group consisting of interleukin 3 (IL-3), interleukin 7 (IL-7), interleukin 12 (IL-12), interleukin 15 (IL-15), interleukin 21 (IL-21), stem cell factor (SCF), and FMS-like tyrosine kinase 3 ligand (Flt3L). It is preferred that IL-3, IL-7, IL-12, IL-15, IL-21, SCF, and Flt3L have human amino acid sequences of them, and they are preferably produced by a recombinant DNA technique in view of safety.

The medium is preferably a serum-free medium. The serum-free medium preferably contains serum albumin, transferrin, and insulin. Serum-free media for culturing lymphocytes are developed and marketed, and they can be used for the present invention. One of the preferred examples of the serum-free medium is a basal medium to which CTS Immune Cell SR (Thermo Fisher Scientific) marketed as a composition for supporting proliferation of human T cells is added. Although the serum albumin contained in the medium may be a human serum albumin or nonhuman animal serum albumin, it is preferably a human serum albumin.

The culture can be performed as feeder-less culture. This is because if feeder cells are used for the culture, there arises a risk of infection in the produced cell population.

Exchange, addition, or supplementation of the medium may be performed at any time after the start of the culture on condition that a desired cell number of NK cells can be obtained, but it is preferably performed every 3 to 5 days.

The culture vessel used for the culture may be a commercially available dish, culture bag, flask, plate, or multiwell plate, but it is not limited to these. Although the culture conditions are not particularly limited on condition that the proliferation effect for NK-like cells is not degraded, culture conditions of 37° C., 5% $CO_2$, and saturated steam atmosphere are common. Culture period is not particularly limited on condition that the cells in the population of NK-like cells are proliferated to a desired cell number. The culture period may be changed depending on the culture conditions. With the culture conditions of 37° C., 5% $CO_2$, and saturated water vapor atmosphere, the culture period may 4 to 15 days. The longest culture period may be about 21 days.

The population of the predetermined NK-like cells obtained by the culture may be a population of $CCR5^+/CCR6^+/CXCR3^+/CD3^-$ cells. The population of the predetermined NK-like cells obtained by the culture may be a population of $CCR5^+/CCR6^+/CXCR3^+/CD31CD11c^+$ cells. The population of the predetermined NK-like cells obtained by the culture may be a population of $CCR5^+/CCR6^+/CXCR3^+/CD31CD11c^+/CD11a^+$ cells. The population of the predetermined NK-like cells obtained by the culture may be a population of $CCR5^+/CCR6^+/CXCR3^+/CD31CD11c^+/CD11a^+/CD18^+$ cells. The population of the predetermined NK-like cells obtained by the culture may be a population of $CCR5^+/CCR6^+/CXCR3^+/CD31CD11c^+/CD11a^+/CD18^-/$integrin $\alpha1^+$ cells. The population of the predetermined NK-like cells obtained by the culture may be a population of $CCR5^+/CCR6^+/CXCR3^+/CD3^-/CD11e/CD11a^+/CD18^+/$integrin $\alpha1^+/$integrin $\alpha3^+$ cells. The population of the predetermined NK-like cells obtained by the culture may be a population of $CCR5^+/CCR6^+/CXCR3^+/CD3^-/CD11c^+/CD11a^+/CD18^+/$integrin $\alpha1^+/$integrin $\alpha3^+/$integrin $\alpha4^+$ cells. The population of the predetermined NK-like cells obtained by the culture may be a population of $CCR5^+/CCR6^+/CXCR3^+/CD3^-/CD11c^+/CD11a^+/CD18^+/$integrin $\alpha1^+/$integrin $\alpha3^+/$integrin $\alpha4^+/$integrin $\alpha5^+$ cells. The population of the predetermined NK-like cells obtained by the culture may be a population of $CCR5^+/CCR6^+/CXCR3^+/CD3^-/CD11e/CD11a^+/CD18^+/$integrin $\alpha1+/$integrin $\alpha3^+/$integrin $\alpha4^+/$integrin $\alpha5^+/ICAM-1^+$ cells. The population of the predetermined NK-like cells obtained by the culture may be a population of $CCR5^+/CCR6^+/CXCR3^+/CD3^+/CD11e/CD11a^+/CD18^+/$integrin $\alpha1^+/$integrin $\alpha3^+/$integrin $\alpha4^+/$integrin $\alpha5^+/ICAM-1^+/$integrin $\beta1^+$ cells. The population of the predetermined NK-like cells obtained by the culture may be a population of $CCR5^+/CCR6^+/CXCR3^+/CD3^-/$integrin $\alpha1^{high}$, $CCR5^+/CCR6^+/CXCR3^+/CD3^-/$integrin $\alpha1^{high}/$integrin $\alpha3^{high}$, $CCR5^+/CCR6^+/CXCR3^+/CD3^-/$integrin $\alpha1^{high}/$integrin $\alpha3^{high}/$integrin $\alpha4^{high}$, $CCR5^+/CCR6^+/CXCR3^+/CD3^-/$integrin $\alpha1^{high}/$integrin $\alpha3^{high}/$integrin $\alpha4^{high}/$integrin $\alpha5^{high}$, $CCR5^+/CCR6^+/CXCR3^+/CD3^-/$integrin $\alpha1^{high}/$integrin $\alpha3^{high}/$integrin $\alpha4^{high}/$integrin $\alpha5^{high}/ICAM-1^{high}$, or $CCR5^+/CCR6^+/CXCR3^+/CD3^-/$integrin $\alpha1^{high}/$integrin $\alpha3^{high}/$integrin $\alpha4^{high}/$integrin $\alpha5^{high}/ICAM-1^{high}/$integrin $\beta1^{high}$ cells. The aforementioned specific NK-like cells included in these populations of NK-like cells may be positive for any one selected from the group consisting of CD16 and CD56 or both of them. For example, the $CCR5^+/CCR6^+/CXCR3^+/CD3^-$ cells included in these populations of NK-like cells may be positive for any one selected from the group consisting of CD16 and CD56 or both of them. The aforementioned specific NK-like cells included in these populations of NK-like cells may be negative for any one selected from the group consisting of CXCR1 and CXCR4 or both of them.

By expression analysis of cell surface antigens of a cell population based on flow cytometry, number of cells expressing each surface antigen can be measured, and therefore ratio of cells expressing each surface antigen (positive ratio) in the cell population can be determined. For example, according to an arithmetic interpretation, if cells expressing a surface antigen A exist in a cell population at a ratio of 50% based on the total cells, and cells expressing a surface antigen B constitute 50% of the total cells, the ratio of cells expressing the surface antigens A and B may be possibly 0%. However, if cells expressing the surface antigen A constitute 90% of the total cells, and cells expressing the surface antigen B constitute 90% of the total cells, there is no possibility that the ratio of cells expressing both the surface antigens A and B in the total cells is 0%.

By the expression analysis for the cell surface antigens of the cell population based on flow cytometry mentioned in Example 1 described later, it was found that there were 92.7% of CCR5-positive cells, 96.3% of CCR6-positive cells, and 51.4% of CXCR3-positive cells in the cell population obtained by the culture. These results indicate that there were CCRS, CCR6 and CXCR3 co-positive cells in the cell population. It was also found that CD11a-positive (high expression) cells and CD11c-positive (high expression) cells existed in the cell population obtained by culture at ratios of 99.8% and 96.8%, respectively. These results indicate that there were CCRS, CCR6, CXCR3, CD11a, and CD11c co-positive cells in the cell population. It was also found that integrin $\alpha1$-positive cells and integrin $\alpha3$-positive cells also existed in the cell population obtained by culture at ratios of 91.0% and 75.3%, respectively. These results indicate that there were CCR5, CCR6, CXCR3, integrin α1 and integrin α3 co-positive cells in the cell population.

Purity for the aforementioned specific NK-like cells in the population of the predetermined NK-like cells obtained by culture (Purity (%)=(Number of the aforementioned NK-like cells)/(Number of total cells)×100) may be 30% or higher. Since it is considered that a higher purity of the specific NK-like cell population provides higher therapeutic effect, the purity is preferably is 30% or higher, 35% or higher, 40% or higher, 45% or higher, or 50% or higher. The purity of the aforementioned specific NK-like cell population may be still higher, and may be 55% or higher, 60% or higher, 65% or higher, 70% or higher, 75% or higher, 80% or higher, 85% or higher, 90% or higher, or 95% or higher.

The population of the predetermined NK-like cells obtained by culture may be a cell population including CCR5-positive, CCR6-positive, CXCR3-positive, and CD3-negative cells, from which cells positive for any selected from the group consisting of CD3, CD4, CD8, CD14, CD19, and CD36 have been removed. The population of the predetermined NK-like cells obtained by culture may include CCR5-positive, CCR6-positive, CXCR3-positive, and CD3-negative cells, in which ratio of cells positive for any selected from the group consisting of CD3, CD4, CD8, CD14, CD19, and CD36 is lower than 10%. The ratio of these cells can be analyzed by flow cytometry. The ratio of the cells positive for any selected from the group consisting of CD3, CD4, CD8, CD14, CD19, and CD36 is preferably lower than 5%, more preferably lower than 2%. This is because it is considered that a higher ratio of the CCR5-positive, CCR6-positive, CXCR3-positive, and CD3-negative cells in the cell population provides a higher tumor cytotoxic activity.

The population of NK-like cells obtained by the production method of the present invention can be said to be a population of enriched NK-like cells in the meaning that a population of the desired $CCR5^+/CCR6^+/CXCR3^+/CD3^-$ NK-like cells have been preferentially cultured and amplified.

The population of the predetermined NK-like cells obtained by culture may include NK cell precursors, T cells, NKT cells, hematopoietic precursor cells, and so forth in addition to the target NK-like cells. After the culture, The target NK-like cells or a population thereof may be selected by using, for example, specific gravity centrifugation, immunomagnetic beads, FACS, flow cytometry, or the like. For example, by using anti-CD3 antibody, anti-CD16 antibody, anti-CD34 antibody, anti-CD36 antibody, anti-CD69 antibody, anti-CD94 antibody, an anti-CD107a antibody, anti-KIR3DL1 antibody, anti-KIR3DL2 antibody, anti-KIR2DL3 antibody, anti-KIR2DL1 antibody, anti-KIR2DS1 antibody, anti-KIR2DL5 antibody, anti-NKp46 antibody, anti-NKp30 antibody, anti-NKG2D antibody, or the like, a population of the target NK-like cells may be selectively separated. The antibody may be a monoclonal antibody, polyclonal antibody, or the like. The selection of a population of the target NK-like cells may be performed by selectively removing T cells, NKT cells, hematopoietic precursor cells, and other cells.

[Use of Population of NK-Like Cells]

The present invention provides a pharmaceutical composition containing the population of NK-like cells, and a pharmaceutically acceptable additive. Examples of the pharmaceutically acceptable additive include, for example, isotonic agent, pH adjustor, buffering agent, stabilizer, cryoprotective agent, antibiotic, and so forth. Specific examples include water, ethanol, sodium chloride, glucose, albumin, and so forth. The population of NK-like cells contained in the pharmaceutical composition of the present invention is preferably the aforementioned population of $CCR5^+/CCR6^+/CXCR3^+/CD3^-$ NK-like cells provided by the present invention. The cell population contained in the pharmaceutical composition of the present invention is preferably a population of NK-like cells showing high tumor cytotoxic activity, more preferably a population of NK-like cells that infiltrate into a solid tumor.

The pharmaceutical composition of the present invention may be administered to a patient having an HLA gene type different from that of the NK-like cells produced by the production method of the present invention.

The pharmaceutical composition is typically in the form of a suspension in which the NK-like cells are suspended in a solution. The solution for suspending the NK-like cells is generally, for example, a cryoprotective solution containing DMSO, physiological saline, phosphate buffered saline (PBS), medium, serum, or the like. The solution may contain a carrier pharmacologically acceptable for drugs and quasi drugs.

The pharmaceutical composition of the present invention may be used for treating an infectious disease or cancer. The pharmaceutical composition of the present invention can also be applied to a treatment of various diseases susceptible to NK-like cells. The pharmaceutical composition of the present invention can also be applied to prevention of various diseases susceptible to NK-like cells. Such diseases include, for example, mouth cancer, gallbladder cancer, bile duct cancer, lung cancer, liver cancer, colon cancer, kidney cancer, vesical cancer, leukemia, infectious diseases caused by viruses, bacteria, or the like, but are not limited to these. The cell therapy of the present invention may be independently performed, or may be performed in combination with a surgical therapy, chemotherapy, radiotherapy, use of an antibody drug, or the like. In the cell therapy using the pharmaceutical composition of the present invention, the NK-like cells may be administered, for example, intravenously, intraarterially, subcutaneously, intraperitoneally, or the like.

The pharmaceutical composition of the present invention can be administered together with an IL-2 preparation. Such an IL-2 preparation may be a genetic recombinant type, and may be teceleukin (genetic recombinant).

Even if the pharmaceutical composition of the present invention is not necessarily used together with an antibody drug, high therapeutic effect thereof can be expected. As one of the known mechanisms of the cytotoxicity by NK cells, antibody-dependent cellular cytotoxicity (ADCC) is known. NK cells have an Fc receptor (CD16) on the cell surfaces, and ADCC is such a mechanism that NK cells bind to an antibody that binds to a target cell via the Fc receptor to injure the target cell. An antibody showing high compatibility with known NK cells and CD16 may be used together, with expecting ADCC activity. However, the population of NK-like cells of the present invention shows high cytotoxic activity even without using an antibody together. It has been found that the population of NK-like cells contained in the pharmaceutical composition of the present invention shows increased chemotaxis to a tumor site compared with a population of NK cells obtained from peripheral blood and not substantially cultured, and infiltrates into a tumor mass. In a cytotoxicity assay, high cytotoxic activities were observed in both of a system in which the population of NK-like cells and an antibody were used together, and a system in which the population of NK-like cells alone was used, but there was no significant difference between them.

This result indicates that the NK-like cells have high cytotoxic activity to tumor cells, even if the ADCC activity is not induced.

The pharmaceutical composition of the present invention may be used together with an antibody drug. Specific examples of antibody that can be used together with the pharmaceutical composition of the present invention include ibritumomabtiuxetan, iodine$^{131}$, catumaxomab, blinatumomab, muromonab-CD3, abciximab, rituximab, basiliximab, infliximab, cetuximab, brentuximab, siltuximab, dinutuximab, obiltoxaximab, daclizumab, palivizumab, trastuzumab, gemtuzumab, alemtuzumab, omalizumab, efalizumab, bevacizumab, natalizumab, tocilizumab, ranibizumab, eculizumab, certolizumabpegol, mogamulizumab, pertuzumab, trastuzumab, obinutuzumab, vedolizumab, pembrolizuma, idarucizumab, mepolizumab, elotuzumab, daratumumab, ixekizumab, reslizumab, adalimumab, panitumumab, golimumab, ustekinumab, canakinumab, ofatumumab, denosumab, ipilimumab, belimumab, raxibacumab, ramucirumab, nivolumab, secukinumab, evolocumab, alirocumab, and necitumumab.

The antibody that can be used together with the pharmaceutical composition of the present invention preferably shows high compatibility to CD16. In the pharmaceutical composition of the present invention, at least a part of the antibody may bind to the NK-like cells.

The pharmaceutical composition of the present invention is preferably produced under conditions conforming to the rules for production control and quality control of drugs and quasi-drugs (Good Manufacturing Practice, GMP) and the criteria for production control and quality control of products for regenerative medicine etc. (Good Gene, Cellular, and Tissue-based Products Manufacturing Practice, GCTP).

The present invention provides use of the population of NK-like cells in manufacture and a drug for use in a treatment of a solid tumor. The present invention provides a population of NK-like cells for use in infiltration into a solid tumor.

The present invention provides a method for treatment or prevention of a solid tumor of a patient, which comprises the step of administrating a therapeutically effective amount of the population of NK-like cells to the patient. Since the population of NK-like cells of the present invention can injure tumor cells of a solid tumor, it is useful for treatment and prevention of a solid tumor of a patient.

The present invention provides a kit for use in the aforementioned treatment or for research use. The kit can include one or more containers such as bag, vial, and tube. The containers can contain the cell population provided by the present invention as a pharmaceutical composition optionally also containing a pharmaceutically acceptable additive. The kit can include a container containing the cell population provided by the present invention in combination with another drug or antibody drug. The kit includes the cell population optionally together with a label or instruction concerning the treatment use or research use described in this specification.

In the present invention, extraction of the whole blood as cord blood or peripheral blood, preparation of autoserum, preparation of mononuclear cells from the whole blood, measurement of cells number of mononuclear cells before and after the culture, measurement of the percentages of NK cells, T cells, hematopoietic precursor cells, and cells of other types among the mononuclear cells before and after the culture, calculation of the amplification magnification of NK-like cells, and statistical analysis about measurement error or significance may be carried out by using any of the methods well known to those skilled in the art.

The examples of the present invention explained below are mentioned only for the purpose of exemplification, and do not limit the technical scope of the present invention. The technical scope of the present invention is defined only by the descriptions of the claims. The present invention may be implemented with any alterations such as addition, deletion and substitution of the elements of the present invention on condition that such alterations do not depart from the scope of the present invention.

EXAMPLES

Example 1

<<Verification of Expression of Chemokine Receptors>>

Peripheral blood of a healthy volunteer was subjected to specific gravity centrifugation for separation, and peripheral blood mononuclear cells (henceforth abbreviated as PBMCs) were obtained. CD3-positive cells were removed from PBMCs by using 5 μL of CliniMACS CD3 (Miltenyi Biotec, catalog number 130-017-601) per 1×10$^7$ cells (the cells collected in this step are referred to as "primary NK"), and the remained cells were cultured. In the culture, the cells were suspended in KBM-501 (Kohjin Bio, containing 5% AB serum) at a density of 5×10$^5$ cells/mL, and cultured for 14 days (the medium was added on the 9th day) by using a 6-well plate (Thermo Fisher Scientific, 140675) or T-75 flask (Thermo Fisher Scientific, 156499). The cells of this cell population are referred to as "14-day cultured cells" or "cells of the present invention".

For analysis of the chemokine receptors, the cells of the present invention after the culture of 14 days and the "primary NK" consisting of the cells collected before the culture as the control were used. The analysis was conducted by flow cytometry, and BD LSRFortessa™ Cell Analyzer (BD Bioscience) was used for it. Fluorescence labeling of the 14-day cultured cells and the primary NK was performed by incubating each type of cells in an antibody solution in which each type of the antibodies shown in Table 1 was suspended in PBS (Wako Pure Chemical Industries) at a final concentration of 1 μg/mL at 2 to 8° C. for 30 minutes in a dark place.

TABLE 1

| antibody name | Cat. | manufacturer | note |
|---|---|---|---|
| FITC anti-human CD181 (CXCR1) antibody | 320605 | Biolegend | chemokine receptor |
| PE/Cy7 anti-human CD182 (CXCR2) antibody | 320715 | Biolegend | chemokine receptor |
| PE anti-human CD183 (CXCR3) antibody | 353705 | Biolegend | chemokine receptor |
| PerCP/Cy5.5 anti-human CD184 (CXCR4) antibody | 306515 | Biolegend | chemokine receptor |
| PE anti-human CD192 (CCR2) antibody | 357205 | Biolegend | chemokine receptor |
| PE anti-human CD194 (CCR4) antibody | 359411 | Biolegend | chemokine receptor |
| PE/Cy7 anti-human CD195 (CCR5) antibody | 359107 | Biolegend | chemokine receptor |
| FITC anti-human CD196 (CCR6) antibody | 353411 | Biolegend | chemokine receptor |
| Pacific Blue™ anti-human CD56 (NCAM) antibody | 318325 | Biolegend | NK cell marker |
| APC/Cy7 anti-human CD3 antibody | 300426 | Biolegend | T cell marker |

The results are shown in FIG. 1A. The cells of the present invention cultured for 14 days strongly expressed chemokine receptors CCR5, CCR6, and CXCR3, and weakly expressed CCR2. They did not express CXCR1 and CXCR2.

It is known that CCR5, CCR6, and CXCR3 are generally contained in immunosuppressive cell populations such as MDSCs (myeloid-derived suppressor cells) and Treg, and these cells abundantly exist in a tumor tissue in a state referred to as cold tumor in living bodies. Since it is considered that the cells of the present invention have the same chemotaxis as that of these cells, it is supposed that they can efficiently infiltrate into a cold tumor, for which immunotherapies are considered to be hardly effective, and can injure it.

The ratios of the CCR5-positive cells, CXCR3-positive cells, and CCR6-positive cells in the 14-day cultured cell population (postcultured) were 92.7%, 96.3%, and 51.4%, respectively (FIG. 1A). Thus, since 92.7%×96.3%× 51.4%=45.88%, the ratio of the CCR5-positive, CCR6-positive, and CXCR3-positive cells in the 14-day cultured cell population is stochastically calculated to be 45.9%.

<<Verification of Expression of Cell Adhesion Molecules>>

For the analysis of cell adhesion molecules, the cells of the present invention cultured for 14 days and the primary NK as the control were used like Example 1. The analysis was performed by flow cytometry. The antibodies used for fluorescence labeling are shown in Table 2. The fluorescence labeling was performed according to the same procedure as mentioned above.

TABLE 2

| antibody name | Cat. | manu-facturer | note |
|---|---|---|---|
| APC anti-human CD11a antibody | 301212 | Biolegend | ICAM-1 |
| APC anti-human CD11b antibody | 301309 | Biolegend | Integrin αM |
| PerCP/Cy5.5 anti-human CD11c antibody | 337210 | Biolegend | Integrin αX |
| PE anti-human CD29 antibody | 303003 | Biolegend | Integrin β1 |
| APC anti-human CD18 antibody | 302113 | Biolegend | Integrin β2 |
| APC anti-human CD61 antibody | 336411 | Biolegend | Integrin β3 |
| PE anti-mouse CD49a antibody | 328303 | Biolegend | Integrin α1 |
| FITC anti-human CD49b antibody | 314306 | Biolegend | Integrin α2 |
| PE anti-human CD49c antibody | 343803 | Biolegend | Integrin α3 |
| PE anti-human CD49d antibody | 304303 | Biolegend | Integrin α4 |
| PE anti-human CD49e antibody | 328009 | Biolegend | Integrin α5 |
| APC anti-human CD31 antibody | 303115 | Biolegend | PECAM-1 |
| Pacific Blue ™ anti-human CD56 (NCAM) antibody | 318325 | Biolegend | NK cell marker |
| APC/Cy7 anti-human CD3 antibody | 300426 | Biolegend | T cell marker |

The results are shown in FIGS. 1C and 1D. The cells of the present invention cultured for 14 days strongly expressed the cell adhesion molecules, ICAM1, integrin α1, LFA-1α, integrin β2, integrin α3, integrin αX, integrin β2, PECAM-1, integrin α5, integrin α4, and integrin β1.

For infiltration into a tumor tissue, adhesion among cells or adhesion of cells with extracellular matrix are required at plurality of key points such as exsorption out of blood vessel, following passage through stroma, adhesion to and invasion into a tumor cell mass, and the cells obtained by the present invention are considered to have an adhesion molecule expression pattern that enables both types of adhesion.

Example 2

<<Contents of CD3-Positive Cells and CD19-Positive Cells>>

In order to analyze contents of CD3-positive cells and CD19-positive cells, the cells of the present invention cultured for 14 days were used like Example 1, and PBMCs were used as the control. The antibodies used for the fluorescence labeling were PE-labeled anti-human CD3 antibody (Biolegend, 300408) and PerCP-Cy5.5-labeled anti-human CD19 antibody (Biolegend, 302230). The fluorescence labeling was performed by the same procedure as that of Example 1.

The results are shown in FIG. 2. The cells of the present invention cultured for 14 days included 0.025% of CD3-positive cells, and 0.28% of CD19-positive cells. On the other hand, PBMCs not cultured included 64.7% of CD3-positive cells, and 8.57% of CD19-positive cells.

Example 3

<<Verification of Infiltration into Solid Tumor Mass>>

Infiltration of the cells of the present invention into IMR32 spheroids as the target was observed.

The IMR32 cells (human MYCN-amplified neuroblastoma cell line) were separated with trypsin-EDTA, $3 \times 10^3$ cells were prepared in 100 μL of RPMI (10% FBS), and the cell suspension was inoculated on EZ-Bind Shut II (registered trademark) microplate (IWAKI, Cat. 4870-800LP), and incubated at 37° C. for 48 to 72 hours to allow formation of IMR32 spheroids. IMR32 spheroids were transferred to a 384-well microplate (film bottom, for high content imaging, CORNING, Cat. 4518) in a number of one spheroid per well by using a 200 μL tip, and incubated at 37° C. for about 1 to 2 hours so that they adhered to the bottom surfaces.

The cells of the present invention used for the cytotoxicity assay of the target cells were induced by the method described in Example 1. The population of NK cells used as the control (referred to as primary NK) was isolated by a treatment of PBMCs separated from peripheral blood of a healthy volunteer by specific gravity centrifugation with EasySep™ Human NK Cell Enrichment Kit (STEMCELL Technologies, Cat. 19055). The cells of the present invention and the primary NK were stained with PKH26 Red Fluorescence Cell Linker Kit (for general cell membranes, SIGMA-ALDOLICH, Cat. PKH26GL, henceforth referred to as PKH26).

To one well of the 384-well microplate to which the IMR32 spheroid was adhered, $1 \times 10^4$ cells/20 μL (KBM-501, 5% AB serum) of the cells of the present invention or primary NK were injected, and incubation was performed at 37° C. for 21 hours to carry out the cytotoxicity assay for IMR32 spheroids. As for the recording of images, after applying the cells of the present invention, primary NK, and anti-GD2 antibody to the IMR32 spheroids, they were photographed at time points of 1, 6, 12, 18 and 21 hours and recorded by using BZ-9000 (KEYENCE). As the anti-GD2 antibody, dinutuximab (Unituxin™, United Therapeutics) was used, and added at a final concentration of 10 μg/mL.

The results are shown in FIG. 3. It can be seen that the cells of the present invention stained with PKH26 invaded into the inside of IMR32 spheroids. The tumor mass including the center part thereof was beginning to collapse after 12 hours from the start of the assay. Although the primary NK stained with PKH26 gathered at the surfaces of the IMR32 spheroids, they did not invade into the inside. Cytotoxic activity of the anti-GD2 antibody (Unituxin (registered trademark)) against IMR32 forming spheroids was not observed under a microscope.

Example 4

<<Verification of Cytotoxic Activity Against Solid Tumor Mass>>

IMR32 spheroids as the target were prepared, and adhered to a 384-well microplate in the same manner as described in Example 3. The cells of the present invention and primary NK were prepared and stained with PHK26 in the same manner as described in Example 3. The cytotoxicity assay for IMR32 spheroids was performed for 5 groups, in which only the cells of the present invention or primary NK was added, the cells of the present invention or primary NK and the anti-GD2 antibody were added, or only the anti-GD2 antibody was added, and a group in which neither the effector cells nor the GD2 antibody was added was prepared as the control. The cells of the present invention or primary NK were added in an amount of $1 \times 10^4$ cells/20 µL (KBM-501, 5% AB serum) per one well of the 384-well microplate to which IMR32 spheroid was adhered. As the anti-GD2 antibody, dinutuximab (Unituxin™, United Therapeutics) was used, and added at a final concentration of 10 µg/mL to the 384-well microplate to which MR32 spheroids were adhered. The cytotoxicity assay was performed by incubation at 37° C. for 21 hours.

After the cytotoxicity assay, centrifugation was performed (500 g, 5 minutes, 4° C.), the supernatant was removed, then a 7-AAD solution (Beckman Coulter, A07704) diluted with PBS was added to suspend the cells, and the suspension was incubated at room temperature for 10 minutes. Measurement was performed with a flow cytometer (BD LSR Fortessa, BD Bioscience), and the results were analyzed with the FlowJo software.

Cytotoxic activity was calculated in accordance with the following equation. It was also similarly calculated in the following examples.

(Cell death of target cells after incubation with effector cells–Natural cell death (negative control))/(Maximum cell death (positive control)–Natural cell death (negative control))×100

The results are shown in FIGS. 4A to 4C. Irrespective of the presence or absence of the anti-GD2 antibody, the cells of the present invention invaded into the inside of the IMR32 spheroids, and the tumor mass including the center part thereof was beginning to collapse (FIG. 4A, lower row). Although the primary NK gathered at the surfaces of the IMR32 spheroids irrespective of the presence or absence of the anti-GD2 antibody, they did not invade into the inside, but it was observed that they more gathered around the IMR32 spheroids in the presence of the anti-GD2 antibody compared with in the absence of the anti-GD2 antibody (FIG. 4A, middle row).

The cells of the present invention showed higher cytotoxic activity compared with the primary NK irrespective of the presence or absence of the anti-GD2 antibody (FIG. 4C).

Example 5

<<Verification of Therapeutic Effect in In Vivo Solid Tumor Model>>

SKOV3 cells, which are cells of a human ovarian cancer cell line introduced with GFP, were cultured in RPMI 1640. The SKOV3 cells (cells of a human ovarian cancer cell line introduced with GFP and cultured in RPMI 1640) were transplanted in an amount of $1 \times 10^5$ cells/200 µL (prepared with PBS) into abdominal cavities of 6 to 7 weeks old NOG mice. The day of the transplantation is defined as day 0. Then, $2.5 \times 10^6$ cells/200 µL (prepared with PBS) of the cells of the present invention or primary NK were intraperitoneally (i.p.) administered on the day 5 (5 days after). Further, 5,000 IU per animal of hIL-2 (Imunace, Shionogi Pharmaceuticals) was administered on the days 5, 6, and 7. The cells and hIL-2 were not administered to the mice of the control group after the day 0. The treatment schedule is shown in FIG. 5.

The mice were euthanized on the day 21, and dissected, the mesentery of each animal was photographed with BZ-9000 (KEYENCE), and the GFP-positive area was quantified with ImageJ. At the time of photographing, the mesentery was extended on a 10-cm dish, an objective lens of two magnifications was used, and all the photographings/analyses were carried out under the fixed conditions (imaging apparatus, imaging area, excitation wavelength, exposure time, and filtering and threshold at the time of analysis). Statistical analysis of the quantified data was conducted by using the JMP software. The analysis was performed by using one-way ANOVA (analysis of variance), and then the Tukey-Kramer method (multiple comparison test).

The results are shown in FIGS. 6A and 6B. While tumor nodes were observed on the mesenteries of the mice not treated or administered with the primary NK, tumor nodes were not observed on the mesentery of the mouse administered with the cells of the present invention. The total density of all the pixels of the GFP-positive area in the mesentery was the highest in the untreated mouse, the secondary highest in the mouse administered with the primary NK, and the lowest in the mouse administered with the cells of the present invention. Although there was no significant difference between the results of the untreated mouse and the mouse administered with the primary NK, a significant difference was observed between the results of the untreated mouse or mouse administered with the primary NK, and the mouse administered with the cells of the present invention ($p<0.01$). These results indicate that the SKOV3 cells transplanted into the immunodeficient mouse were disappeared by the administration of the cells of the present invention. The therapeutic effect of the cells of the present invention in the in vivo solid tumor model was thus confirmed.

Example 6

<<Improved Method for Producing Cell Population>>

Cells were prepared, and three types of cell populations were prepared as described below.
1) Mixture (1:1) of cells prepared by the methods of the paragraphs 2) and 3) mentioned below (henceforth referred to as "NK-like +mono").
2) Cells prepared by removing CD2, CD3, CD19, CD20, CD56, CD66b, CD123, and a glycophorin A-positive cells from PBMCs by using EasySep™ Human Monocyte Enrichment Kit WITHOUT CD16 DEPLETION (STEMCELL, Cat. 19058), then suspending the remaining cells in KBM-501 (5% AB serum) at a density of $5 \times 10^5$ cells/mL, and culturing the cells for 14 days in Nunc Easy Flask 75 FILIT NUNCLON DSI (Thermo Fisher Scientific, Cat. 156944) or on Nunc MULTIDISH 6 NUNCLON DELTA SI (Thermo Fisher Scientific, Cat. 140675) (henceforth referred to as "enriched mono".
3) Cells prepared by removing CD3, CD4, CD14, CD19, CD20, CD36, CD66b, CD123, HLA-DR, and glycophorin A-positive cells from PBMCs by using EasySep™ NK Cell Enrichment Kit (STEMCELL, Cat. 19055), then suspending the remaining cells in KBM-501 (5% AB serum) at a density of $5 \times 10^5$ cells/mL, and incubating the cells for 14 days in Nunc Easy Flask 75 FILIT NUN- CLON DSI (Thermo Fisher Scientific, Cat. 156944) or on Nunc MULTIDISH 6 NUNCLON DELTA SI (Thermo Fisher Scientific, Cat. 140675) (henceforth referred to as "enriched NK-like".

The photographs of the cells on the 10th day after the start of the culture are shown in FIG. 7. In the two groups other than the enriched mono group, many cells having a typical activated lymphocyte-like form were confirmed. For the enriched mono group, many large-sized strongly adhering myelocyte type cells were confirmed, and comparatively small floating cells can also be confirmed. The culture conditions were favorable for all the groups, proliferation in KBM-501 was appropriately achieved, and any conspicuous apoptosis was not seen.

<<Measurement of Cytotoxic Activity and Measurement of CD107a-Positive Ratio>>

K562 cells (human chronic myeloid leukemia cell line) were prepared at a density of $1 \times 10^6$ cells/mL in the RPMI 1640 medium (Wako Pure Chemical Industries, 189-02025) containing 10% FBS (NICHIREI Bioscience, 171012-500ML), 100 units of penicillin, and 100 µg/mL of streptomycin (Nacalai Tesque, 26253-84) (henceforth referred to as 10%FBS/RPMI1640). The prepared K562 cells were stained by using PKH26 Red Fluorescent Cell Linker Kit (Sigma), and prepared at a density of $2 \times 10^6$ cells/mL.

Groups consisting of each one of the aforementioned three types of cell populations (NK-like+mono, enriched NK-like, and enriched mono), and the population of the K562 cells, groups consisting of only each one of the aforementioned three types of cell populations (NK-like+mono, enriched NK-like, and enriched mono), group consisting of only the K562 cells as the negative control, and group consisting of the K562 cells fixed with 10% formalin as the positive control were prepared.

Any one type of the aforementioned three types of cell populations (NK-like+mono, enriched NK-like, and enriched mono) and the K562 cells were added to each well of a 96-well plate at a cell number ratio of 1:1, mixed, and allowed to react at 37° C. for 2 hours. The experimental procedure consisted of first adding the K562 cells to the plate, then adding 200 µg/mL of APC-labeled anti-human CD107a antibody* (Biolegend, 328620) at a final concentration of 1 µg/mL, and finally adding one of the aforementioned three types of cell populations (NK-like+mono, enriched NK-like, and enriched mono). After the culture, centrifugation (500 g, 5 minutes, 4° C.) was performed, the supernatant was removed, then a 7-AAD solution (Beckman Coulter, A07704) diluted with PBS was added to suspend the cells, the suspension was incubated at room temperature for 10 minutes, and then the cells were washed. Measurement was performed by using a flow cytometer (BD LSR Fortessa, BD Bioscience), and analysis was performed by using the FlowJo software.

*Since CD107a exists in the granules contained in NK cells, and migrates to the cell membrane surfaces at the time of degranulation (release of perforin and granzyme), positivity for CD107a indirectly indicates that NK attacked the object.

The results are shown in FIGS. 8A and 8B. The NK-like+mono cell population and the enriched NK-like cell population showed high cytotoxic activity.

<<Verification of Expression of Chemokine Receptors>>

An experiment was performed for expressions of chemokine receptors CCR4, CCR5, CCR6, CXCR3, and CXCR4 in the NK-like cells produced by the improved production method described in this example (method using enriched NK-like cell population and NK-like+mono cell population as materials) according to the procedure described in Example 1.

The results are shown in FIG. 9. By the improved production method of this example, a cell population including CCR5-positive, CCR6-positive, and CXCR3-positive cells could be obtained. It was also found that expression property for CCR6 may differ depending on the donor.

The invention claimed is:

1. A cell population comprising cells each being CCR5-positive, CCR6-positive, CXCR3-positive, and CD3-negative.

2. The cell population according to claim 1, wherein the CCR5-positive, CCR6-positive, CXCR3-positive, and CD3-negative cells further highly express CD11a and highly express CD11c, and these highly expressing properties are judged by comparison with expressions in a population of NK cells obtained from peripheral blood and not substantially cultured.

3. The cell population according to claim 1, wherein the CCR5-positive, CCR6-positive, CXCR3-positive, and CD3-negative cells are further integrin α1-positive, integrin α3-positive, and integrin β3-negative.

4. The cell population according to claim 1, wherein ratio of the CCR5-positive, CCR6-positive, CXCR3-positive, and CD3-negative cells is 30% or higher in the cell population.

5. The cell population according to claim 1, wherein ratio of cells positive for any selected from the group consisting of CD3 and CD19 is lower than 5%.

6. The cell population according to claim 1, wherein cells positive for any selected from the group consisting of CD4, CD8, CD14, CD19, and CD36 have been removed from the cell population.

7. A pharmaceutical composition, which contains the cell population according to claim 1, and a pharmaceutically acceptable additive.

8. A method for treating or preventing a solid tumor, comprising a step of administering the cell population according to claim 1 or the pharmaceutical composition according to claim 7 to a human.

9. The method according to claim 8, wherein the cells that are CCR5-positive, CCR6-positive, CXCR3-positive, and CD3-negative are administered in such a manner that the cells infiltrate in the solid tumor.

10. A method for treating or preventing an infectious disease, comprising a step of administering the cell population according to claim 1 or the pharmaceutical composition according to claim 7 to a human.

11. A method for treating or preventing a cancer, comprising a step of administering the cell population according to claim 1 or the pharmaceutical composition according to claim 7 to a human.

12. The method according to claim 11, wherein the cancer is selected from the group consisting of mouth cancer, gallbladder cancer, bile duct cancer, lung cancer, liver cancer, colon cancer, kidney cancer, vesical cancer, and leukemia.

* * * * *